(12) United States Patent
Wang et al.

(10) Patent No.: US 12,372,503 B2
(45) Date of Patent: Jul. 29, 2025

(54) MULTIFUNCTIONAL MAGNETIC TAGS FOR MUD LOGGING

(71) Applicant: Saudi Arabian Oil Company, Dhahran (SA)

(72) Inventors: Wei Wang, Quincy, MA (US); Sehoon Chang, Boston, MA (US); Hooisweng Ow, Woburn, MA (US)

(73) Assignee: Saudi Arabian Oil Company, Dhahran (SA)

( * ) Notice: Subject to any disclaimer, the term of this patent is extended or adjusted under 35 U.S.C. 154(b) by 133 days.

(21) Appl. No.: 18/465,669

(22) Filed: Sep. 12, 2023

(65) Prior Publication Data

US 2023/0417712 A1  Dec. 28, 2023

Related U.S. Application Data

(62) Division of application No. 17/454,176, filed on Nov. 9, 2021, now Pat. No. 11,796,517.

(51) Int. Cl.
*G01N 30/72* (2006.01)
*E21B 47/11* (2012.01)
(Continued)

(52) U.S. Cl.
CPC .......... *G01N 30/7206* (2013.01); *E21B 47/11* (2020.05); *E21B 49/08* (2013.01);
(Continued)

(58) Field of Classification Search
None
See application file for complete search history.

(56) References Cited

U.S. PATENT DOCUMENTS

| | | |
|---|---|---|
| 4,772,563 A | 9/1988 | Evangelista et al. |
| 5,124,268 A | 6/1992 | Dakubu |

(Continued)

FOREIGN PATENT DOCUMENTS

| | | |
|---|---|---|
| EP | 0171978 | 11/1990 |
| EP | 1721603 | 11/2006 |

(Continued)

OTHER PUBLICATIONS

U.S. Appl. No. 17/454,176, filed Nov. 9, 2021, Wang et al.

(Continued)

*Primary Examiner* — Xiaoyun R Xu
(74) *Attorney, Agent, or Firm* — Fish & Richardson P.C.

(57) ABSTRACT

Compositions and methods for determining the origin location of a subterranean sample are provided. Compositions include a nanoparticle tag including a superparamagnetic iron oxide core, an intermediate layer including a fluorescent dye, and a polymer shell. The nanoparticles can be synthesized by functionalizing a superparamagnetic iron oxide nanoparticle core and covalently bonding a fluorescent dye to the functionalized nanoparticle core. In some implementations, a polymer is covalently bonded to the functionalized, fluorescent superparamagnetic iron oxide nanoparticle core. The nanoparticle tag can be used to determine the origin location of a subterranean sample by mixing the nanoparticle tag into a fluid, flowing the fluid into a subterranean formation, recovering subterranean samples from the subterranean formation, and separating tagged samples from untagged samples using a magnet. The origin location of the subterranean sample can be determined by analyzing the fluorescent signal of the nanoparticle tag.

20 Claims, 14 Drawing Sheets

(51) Int. Cl.
*E21B 49/08* (2006.01)
*G01N 21/64* (2006.01)
*G01N 33/24* (2006.01)
*G01N 30/02* (2006.01)

(52) U.S. Cl.
CPC ......... *G01N 21/6428* (2013.01); *G01N 33/24* (2013.01); *G01N 2021/6439* (2013.01); *G01N 2030/025* (2013.01)

(56) References Cited

U.S. PATENT DOCUMENTS

| | | |
|---|---|---|
| 5,168,927 A | 12/1992 | Stegenneier |
| 6,250,848 B1 | 6/2001 | Moridis et al. |
| 6,590,647 B2 | 7/2003 | Stephenson |
| 6,691,780 B2 | 2/2004 | Nguyen et al. |
| 7,032,662 B2 | 4/2006 | Malone |
| 7,485,471 B1 | 2/2009 | Sun et al. |
| 7,588,827 B2 | 9/2009 | Nie et al. |
| 7,879,625 B1 | 2/2011 | Boss |
| 8,269,501 B2 | 9/2012 | Schmidt et al. |
| 8,337,783 B2 | 12/2012 | Locascio et al. |
| 8,627,902 B2 | 1/2014 | Hammer |
| 8,638,104 B2 | 1/2014 | Barber et al. |
| 8,877,954 B2 | 11/2014 | Giesenberg et al. |
| 9,080,097 B2 | 7/2015 | Gupta et al. |
| 9,133,709 B2 | 9/2015 | Huh et al. |
| 9,366,099 B2 | 6/2016 | Ly |
| 10,273,399 B2 | 4/2019 | Cox |
| 10,308,865 B2 | 6/2019 | Cox |
| 10,308,895 B2 | 6/2019 | Vidal et al. |
| 10,487,259 B2 | 11/2019 | Cox |
| 2003/0220204 A1 | 11/2003 | Baran et al. |
| 2004/0108110 A1 | 6/2004 | Zupanick et al. |
| 2005/0252286 A1 | 11/2005 | Ibrahim et al. |
| 2006/0105052 A1 | 5/2006 | Acar et al. |
| 2006/0293430 A1 | 12/2006 | Wang et al. |
| 2007/0114030 A1 | 5/2007 | Todd et al. |
| 2008/0110253 A1 | 5/2008 | Stephenson et al. |
| 2008/0111064 A1 | 5/2008 | Andrews et al. |
| 2009/0087911 A1 | 4/2009 | Rogerio |
| 2009/0087912 A1 | 4/2009 | Ramos et al. |
| 2009/0248309 A1 | 10/2009 | Nelville et al. |
| 2009/0277625 A1 | 11/2009 | Bai et al. |
| 2010/0049625 A1 | 2/2010 | Biebesheimer et al. |
| 2010/0092865 A1 | 4/2010 | Kanno et al. |
| 2010/0224823 A1 | 9/2010 | Yin et al. |
| 2010/0307745 A1 | 12/2010 | Lafitte et al. |
| 2011/0012331 A1 | 1/2011 | Kim |
| 2011/0030949 A1 | 2/2011 | Weaver et al. |
| 2011/0207231 A1 | 8/2011 | Natan et al. |
| 2011/0239754 A1 | 10/2011 | Dyer et al. |
| 2011/0257887 A1 | 10/2011 | Cooper et al. |
| 2011/0260051 A1 | 10/2011 | Preudhomme et al. |
| 2011/0275061 A1 | 11/2011 | Weidemaier et al. |
| 2012/0062886 A1 | 3/2012 | Piotti et al. |
| 2012/0115128 A1 | 5/2012 | Miller |
| 2012/0135080 A1 | 5/2012 | Bromberg et al. |
| 2012/0193578 A1 | 8/2012 | Pan et al. |
| 2012/0257199 A1 | 10/2012 | Liu et al. |
| 2012/0261617 A1 | 10/2012 | Pan et al. |
| 2012/0325465 A1 | 12/2012 | Hammer et al. |
| 2013/0040292 A1 | 2/2013 | Lopez et al. |
| 2013/0078469 A1 | 3/2013 | Winter et al. |
| 2013/0084643 A1 | 4/2013 | Commarieu et al. |
| 2013/0087329 A1 | 4/2013 | Hewitt et al. |
| 2013/0109261 A1 | 5/2013 | Koene |
| 2013/0244914 A1 | 9/2013 | Wu et al. |
| 2013/0259808 A1 | 10/2013 | Chen et al. |
| 2013/0296453 A1 | 11/2013 | Giesenberg et al. |
| 2013/0312970 A1 | 11/2013 | Lafitte et al. |
| 2013/0341030 A1 | 12/2013 | Brannon et al. |
| 2014/0060832 A1 | 3/2014 | Mahoney et al. |
| 2014/0077121 A1 | 3/2014 | Sun et al. |
| 2014/0120627 A1 | 5/2014 | Rubino et al. |
| 2014/0186939 A1 | 7/2014 | Peterman et al. |
| 2014/0190700 A1 | 7/2014 | Tang et al. |
| 2014/0231077 A1 | 8/2014 | Rivero et al. |
| 2014/0260694 A1 | 9/2014 | Szlendak |
| 2014/0323363 A1 | 10/2014 | Perriat |
| 2014/0360973 A1 | 12/2014 | Yin et al. |
| 2015/0013983 A1 | 1/2015 | Alwattari |
| 2015/0038347 A1 | 2/2015 | Johnson et al. |
| 2015/0050741 A1 | 2/2015 | Tour et al. |
| 2015/0079270 A1 | 3/2015 | Wang et al. |
| 2015/0118501 A1 | 4/2015 | Lu |
| 2015/0132543 A1 | 5/2015 | Nouzille et al. |
| 2015/0159079 A1 | 6/2015 | Huh et al. |
| 2015/0232747 A1 | 8/2015 | Kanj et al. |
| 2015/0268370 A1 | 9/2015 | Johnston et al. |
| 2015/0368547 A1 | 12/2015 | Lesko et al. |
| 2015/0376493 A1 | 12/2015 | Huh et al. |
| 2016/0003040 A1 | 1/2016 | Jessheim et al. |
| 2016/0040514 A1 | 2/2016 | Rahmani et al. |
| 2016/0083641 A1 | 3/2016 | Gamage |
| 2016/0097750 A1 | 4/2016 | Van Herzen et al. |
| 2016/0186044 A1 | 6/2016 | Rothrock et al. |
| 2016/0215030 A1 | 7/2016 | Bressner |
| 2016/0264846 A1 | 9/2016 | Bennetzen et al. |
| 2016/0304934 A1 | 10/2016 | Matsuno |
| 2017/0022804 A1 | 1/2017 | Gupta et al. |
| 2017/0059668 A1 | 3/2017 | Chang et al. |
| 2017/0199124 A1 | 7/2017 | Bolduc et al. |
| 2017/0350236 A1 | 12/2017 | Shen et al. |
| 2018/0171782 A1 | 6/2018 | Cox et al. |
| 2018/0265635 A1 | 9/2018 | Khamatnurova et al. |
| 2018/0275114 A1 | 9/2018 | Kosynkin et al. |
| 2019/0118265 A1 | 4/2019 | Nie et al. |
| 2019/0218907 A1 | 7/2019 | Ow et al. |
| 2019/0226326 A1 | 7/2019 | Ow et al. |
| 2019/0368336 A1 | 12/2019 | Hammond et al. |
| 2019/0382648 A1 | 12/2019 | Murugesan et al. |
| 2021/0025858 A1 | 1/2021 | Ow et al. |
| 2022/0305472 A1 | 9/2022 | Baker et al. |
| 2023/0141596 A1 | 5/2023 | Wang et al. |
| 2023/0141819 A1 | 5/2023 | Wang et al. |
| 2023/0144199 A1 | 5/2023 | Wang et al. |
| 2023/0148198 A1 | 5/2023 | Wang et al. |

FOREIGN PATENT DOCUMENTS

| | | |
|---|---|---|
| EP | 2040075 | 3/2009 |
| EP | 2480625 | 4/2013 |
| EP | 2480626 | 4/2013 |
| GB | 2489714 | 10/2012 |
| JP | 2005524849 | 8/2005 |
| JP | 2007514169 | 5/2007 |
| JP | 2008505259 | 2/2008 |
| JP | 2008524602 | 7/2008 |
| JP | 2009535060 | 10/2009 |
| JP | 2009540326 | 11/2009 |
| JP | 2015523073 | 8/2015 |
| WO | WO 2010138914 | 12/2010 |
| WO | WO 2011035292 | 3/2011 |
| WO | WO 2011035294 | 3/2011 |
| WO | WO 2011063023 | 5/2011 |
| WO | WO 2012154332 | 11/2012 |
| WO | WO 2012158478 | 11/2012 |
| WO | WO 2013142869 | 9/2013 |
| WO | WO 2014014919 | 1/2014 |
| WO | WO 2014066793 | 5/2014 |
| WO | WO 2014207075 | 12/2014 |
| WO | WO 2015044446 | 4/2015 |
| WO | WO 2015058206 | 4/2015 |
| WO | WO 2015097116 | 7/2015 |
| WO | WO 2015200060 | 12/2015 |
| WO | WO 2016015027 | 1/2016 |
| WO | WO 2016087397 | 6/2016 |
| WO | WO 2017011328 | 1/2017 |
| WO | WO 2017136641 | 8/2017 |
| WO | WO 2017164822 | 9/2017 |

(56) References Cited

FOREIGN PATENT DOCUMENTS

| | | |
|---|---|---|
| WO | WO 2018085504 | 5/2018 |
| WO | WO 2018175763 | 9/2018 |

OTHER PUBLICATIONS

Agenet et al., "SPE 157019: Fluorescent Nanobeads: a First Step Toward Intelligent Water Tracers" Society of Petroleum Engineers, SPE International Oilfield Nanotechnology conference, Jun. 12-14, 2012, 13 pages.

Anisimov, "SPE 118862: The Use of Tracers for Reservoir Characterization" Society of petroleum Engineers (SPE), presented at SPE Middle East Oil and Gas Show and Conference, Mar. 15-18, 2009, 8 pages.

Armelao et al., "Design of luminescent lanthanide complexes: From molecules to highly efficient photo-emitting materials" Coordination Chemistry Reviews, vol. 254, Mar. 5-6, 2010, 19 pages.

Aslan et al., "Fluorescent Core—Shell AG@$SiO_2$ Nanocomposites for Metal-Enhanced Fluorescence and Single Nanoparticle Sensing Platforms" Jan. 19, 2007, 2 pages.

Badgett et al., "Totalsynthese eines Neobetanidin-Derivates und des Neobetenamins" Helvetica Chimica Acta, 1970, 53(2): 433-448, 16 pages (English Abstract).

Bagaria et al., "Iron Oxide Nanoparticles Grafted with Sulfonated Copolymers are Stable in Concentrated Brine at Elevated Temperatures and Weakly Adsorb on Silica" ACS Applied Materials & Interfaces, vol. 5, No. 8, Mar. 25, 2013, 3329-3339, 11 pages.

Bala et al., "Interaction of Different Metal Ions with Carboxylic Acid Group: A Quantitative Study" The Journal of Physical Chemistry A, vol. 111, No. 28, Jun. 2007, 6183-6190, 8 pages.

Bao et al., "Luminescence properties of the co-luminescence groups of Sm—La-pyridyl carboxylic acids" Journal of Rare Earths, 30(4), Apr. 2012, 320-324, 5 pages.

Blachier et al., "Adsorption of polyamine on clay minerals" Journal of Colloid and Interface Science, 336, Aug. 2009, 599-606, 8 pages.

Borrini et al., "Water Soluble PDCA Derivatives for Selective Ln(III)/An(III) and Am(III)/Cm(III) Separation" Solvent Extraction and Ion Exchange, 33(3), Oct. 2014, 224-235, 30 pages.

Brichart et al., "The Use of Fluorescent Tracers for Inhibitor Concentration Monitoring Useful for Scale Inhibitor" International Petroleum Technology Conference, IPTC-17933-MS, presented at the International Petroleum Technology Conference held in Kuala Lumpur, Malaysia, Dec. 10-12, 2014, 8 pages.

Bunzil et al., "Taking advantage of luminescent lanthanide ions" Chemical Society Reviews, Dec. 2005, 29 pages.

Chang et al., "Magnetic SERS Composite Nanoparticles for Microfluidic Detection" 251st ACE National Meeting, Mar. 13-17, 2016, 1 page.

Chen et al., "Aggregation Kinetics of Alginate-Coated Hematite Nanoparticles in Monovalent and Divalent Electrolytes" Environmental Science & Technology, vol. 40, No. 5, Mar. 2006, 1516-1523, 9 pages.

Chen et al., "Analysis of the solution conformations of T4 lysozyme by paramagnetic NMR spectroscopy" Physical Chemistry Chemical Physics, 2016, 18(8), 5850-5859, 10 pages.

Chen et al., "Impact of Irreversible Retention on Tracer Deployments; Constraining Novel Material Deployments" SPE 188890-MS, in SPE Abu Dhabi International Petroleum Exhibition and Conference, Society of Petroleum Engineers, Nov. 2017, 8 pages.

Chen et al., "Improved Reservoir History Matching and Prudction Optimization with Tracer Data" SPE 191523-MS, in SPE Annual Technical Conference and Exhibition, Society of Petroleum Engineers, Sep. 2018, 15 pages.

Chen et al., "Upconversion Nanoparticles: Design, Nanochemistry, and Applications in Theranostics" Chem. Rev, 114(10), Mar. 2014, 5161-5214, 54 pages.

Chen et al., "FITC functionalized magnetic core-shell $Fe_3O_4$/Ag hybrid nanoparticle for selective determination of molecular biothiols" Elsevier Ltd., Dec. 2013, 7 pages.

Chen et al.; "Hydration Repulsion between Carbohydrate Surfaces Mediated by Temperature and Specific Ions" Scientific Reports, vol. 6, Jun. 23, 2016, 10 pages.

Cheraghian, "Application of nano-particles of clay to improve drilling fluid" Int. J. Nanosci. Nanotechnol., Jun. 13, 2017, 177-186, 10 pages.

Chuang et al., "Ultra-sensitive in-situ detection of novel near-infrared persistent luminescent tracer nanoagents in crude oil-water mixtures" a natureresearch journal, Scientific Reports, Jun. 15, 2016, 5 pages.

Coates et al, "Enhancement of luminescence of europium(m) ions in water by use of synergistic chelation. Part 1.1 : 1 and 2 : 1 complexes" J. Chem. Soc, Perkin Trans., Jan. 1996, 1275-1282, 8 pages.

Cole et al.; "Polyethylene Glycol Modified, Cross-Linked Starch-Coated Iron Oxide Nanoparticles for Enhanced Magnetic tumor Targeting" Biomaterials, vol. 32, No. 8, Mar. 1, 2011, 2183-2193, 11 pages.

Cox et al., "Pyrolyzable Nanoparticle Tracers for Environmental Interrogation and Monitoring" ACS Appl. Mater. Interfaces, 2017, 9(15), 13111-13120, 10 pages.

Cubillos et al., "SPE 174394-MS: The Value of Inter-well and Single Well Tracer Technology for De-Risking and Optimizing a CEOR Process—Caracara Field Case" Society of Petroleum Engineers (SPE), presented at EUROPEC 2015, Jun. 1-4, 2015, 19 pages.

Das et al., "Molecular Fluorescence, Phosphorescence, and Chemiluminescence Spectrometry" Analytical Chemistry, Nov. 3, 2011, 29 pages.

Deans, "SPE 7076: Using Chemical Tracers To Measure Fractional Flow And Saturation In-Situ" Society of Petroleum Engineers (SPE), presented at SPE Symposium on improved Methods of Oil Recovery, Apr. 16-17, 1978, 10 pages.

Deschamps et al., "Drilling to the Extreme: the Micro-Coring Bit Concept" IADC/SPE 115187, presented at the IADC/SPE Asai Pacific Drilling Technology Conference and Exhibition, Aug. 25-27, 2008, 12 pages.

Desmette et al., "Drilling Hard and Abrasive Rock Efficiently, or Generating Quality Cuttings? You No Longer Have to Choose . . . " SPE 116554, Society of Petroleum Engineers, 2008 SPE Annual Technical Conference and Exhibition, Sep. 21-24, 2008, 19 pages.

Du et al., "SPE 93140: Interwell Tracer Tests: Lessons Learned from past Field Studies" Society of Petroleum Engineers (SPE), presented at SPE Asia Pacific Oil and Gas Conference and Exhibition, Apr. 5-7, 2005, 9 pages.

Dugstad, "Chapter 6: Well-to-well tracer tests" in Petroleum Engineering Handbook, 2007, 651-683, 31 pages.

Dung et al., "Structural and magnetic properties of starch coated magnetite nanoparticles" Journal of Experimental Nanoscience, Sep. 4, 2009, 259-267, 9 pages.

Edwards et al., "Extending the distance range accessed with continuous wave EPR with Gd3+ spin probes at high magnetic fields" Physical Chemistry Chemical Physics, 15(27), 2013, 11313-11326, 14 pages.

El-Aneed et al., "Mass Spectrometry, Review of the Basics: Electrospray, MALDI, and Commonly Used Mass Analyzers" Applied Spectroscopy Reviews, Mar. 16, 2009, 22 pages.

Fichtel et al., "A highly sensitive HPLC method for determination of nanomolar concentrations of dipicolinic acid, a characteristic constituent of bacterial endospores" Journal of Microbiological Methods, 2007, 70, 319-327, 9 pages.

Freeze and Cherry, "Chapter 9: Groundwater Contamination" in Groundwater, Englewood Cliffs, NJ: Prentice-Hall, Inc., 1979, 80 pages.

Galdiga and Greibrokk, "Ultra-trace determination of flurinated aromatic carboxylic acids in aqueous reservoir fluids using solid-phase extraction in combination with gas chromatography-mass spectrometry" Journal of Chromatography, vol. 793, Issue 2, Apr. 1997, 297-306, 10 pages.

Gao et al., "A Surface Functional Monomer-Directing Strategy for Highly Dense Imprinting of TNT at Surface of Silica Nanoparticles" Journal of American Chemical Society, vol. 129, No. 25, Jun. 2007, 7859-7866, 8 pages.

(56) References Cited

OTHER PUBLICATIONS

Gardiner et al., "Practical Raman Spectroscopy" Springer-Verlag, 1989, 9 pages.
Ge et al., "Fluorescence modified chitosan coated magnetic nanoparticles for high-efficient cellular imaging" Nanoscale Res. Lett, 4, Jan. 2009, 287-295, 9 pages.
George et al., "Modified Dipicolinic Acid Ligands for Sensitization and Europium (III) Luminescence" Inorganic Chemistry, vol. 45, No. 4, Feb. 1, 2006, 6 pages.
Georgi, et al., "Advances in Cuttings Collection and Analysis" SPWLA 34th Annual Logging Symposium, Jun. 13-16, 1993, 20 pages.
Gordon-Grossman et al., "W-Band pulse EPR distance measurements in peptides using Gd3+-dipicolinic acid derivatives as spin labels" Physical Chemistry Chemical Physics, 13(22), 2011, 10771-10780, 10 pages.
Grutzke et al., "Heptacoordinate Heteroleptic Salan (ONNO) and Thiosalan (OSSO) Titanium(IV) Complexes: Investigation of Stability and Cytotoxicity" Inorganic Chemistry 54(14), Jul. 2015, 6697-6706, 10 pages.
Hagoot, "The response of interwell tracer tests in watered-out reservoirs" SPE 11131-MS, in SPE Annual Technical Conference and Exhibition, Society of Petroleum Engineers, Jan. 1982, 21 pages.
Han et al., "Application of Silver-Coated Magnetic Microspheres to a SERS-Based Optofluidic Sensor" The Journal of Physical Chemistry (JPCC), Mar. 7, 2011, 7 pages.
Hardy et al., "A novel fluorescent tracer for real-time tracing of clay transport over soil surfaces" Catena, 141, Jun. 2016, 39-45, 7 pages.
He et al., "Luminescent Europium Chelates Synthesis and Fluorescence Properties" Sensors and Materials (2007), 19(2), 123-132, 10 pages.
Hindle et al., "Dipicolinic acid (DPA) assay revisited and appraised for spore detection" Analyst, 1999, 124: 1599-1604, 6 pages.
Hu et al., "Smart Liquid SERS Substrates based on $Fe_3O_4$/Au Nanoparticles with Reversibility Tunable Enhancement Factor for Practical Quantitative Detection" a nature research journal, Scientific Reports, Nov. 27, 2014, 10 pages.
Huseby et al., "Assessing EOR potential from partitioning tracer data" SPE 172808-MS, in SPE Middle East Oil and Gas Show and Conference, Society of Petroleum Engineers, Mar. 2015, 15 pages.
Huseby et al., "SPE-169183-MS: High Quality Flow Information from Tracer Data" Society of Petroleum Engineers (SPE), presented at the SPE Bergen One Day Seminar, Apr. 2, 2014, 9 pages.
Hutchins et al., "SPE-21049: Aqueous Tracers for Oilfield Applications" Society of Petroleum Engineers (SPE), presented at SPE International Symposium on Oilfield Chemistry, Feb. 20-22, 1991, 9 pages.
Invitrogen, "Fluorophores and Their Amine-Reactive Derivatives" Molecular Probs Handbook, A Guide to Fluorescent Probes and Labeling Technologies, 11th Edition, 2010, 88 pages.
Jenkins et al., "Ultratrace Determination of Selected Lanthanides by Luminescence Enhancement" Analytical Chemistry, vol. 68, No. 17, Jan. 1, 1996, 7 pages.
Jun et al., "Multifunctional Silver-Embedded Magnetic Nanoparticles as SERS Nanoprobes and Their Applications" Wiley-VCH Verlag GmbH& Co. KGaA, Weinheim, Jan. 4, 2010, 7 pages.
Kaewsaneha et al., "Immobilization of fluorescein isothiocyanate on magnetic polymeric nanoparticle using chitosan as spacer," Journal of Colloid and Interface Science, 2012, 377:145-152, 8 pages.
Kaushik et al., "Gd(III) and Mn(II) complexes for dynamic nuclear polarization: small molecular chelate polarizing agents and applications with site-directed spin labeling of proteins" Physical Chemistry Chemical Physics, 18(39), 2016, 27205-27218, 36 pages.
Khan et al., "Optimizing waterflood management in a giant UAE carbonate oil field using simulation-based streamlines" SPE 171777-MS, in Abu Dhabi International Petroleum Exhibition and Conference, Society of Petroleum Engineers, Nov. 10-13, 2014, 9 pages.
Kneipp et al., "Single Molecule Detection Using Surface-Enhanced Raman Scattering (SERS)" Physical Review Letters, American Physical Society vol. 78, No. 9, Mar. 3, 1997, 4 pages.
Kornberger and Thiele, "Experiences with an Efficient Rate-Management Approach for the 8th Tortonian Reservoir in the Vienna Basin" SPE 166393-PA, SPE Reservoir Evaluation and Engineering, vol. 17, No. 2, May 2014, 12 pages.
Kosynkin and Alaskar, "Oil Industry First Interwell Trial of Reservoir Nanoagent Tracers" SPE 181551-MS, in SPE Annual Technical Conference and Exhibition, Society of Petroleum Engineers, Sep. 2016, 15 pages.
Kramer, "Water-Soluble Dendritic Architectures with Carbohydrate Shells for the Templation and Stabilization of Catalytically Active Metal Nanoparticles" published by ACS, Macromolecules, vol. 38, No. 20, Aug. 27, 2005, 8308-8315, 8 pages.
Labbe et al., "Development of metal-chelating inhibitors for the Class II fructose 1,6-bisphosphate (FBP) aldolase" Journal of Inorganic Biochemistry, 112, Jul. 2012, 49-58, 10 pages.
Lachowicz et al., "Biocompatible and fluorescent superparamagnetic iron oxide nanoparticles with superior magnetic properties coates with charged polysaccharide derivatives" Colloids and Surfaces B: Biointerfaces, 2017, 150, 402-407, 18 pages.
Larsen et al, "Efficient Synthesis of 4,7-Diamino Substituted 1,10-Phenanthroline-2,9-dicarboxamides" Organic Letters, vol. 13, No. 13, Jul. 2011, 3546-3548, 3 pages.
Li et al., "Long persistent phosphors—from fundamentals to applications" Chem. Soc. Rev., 45(8), Apr. 2016, 2090-2136, 48 pages.
Li et al., "Magic Angle Spinning NMR Structure Determination of Proteins from Pseudocontact Shifts" Journal of the American Chemical Society, 135(22), May 2013, 8294-8303, 10 pages.
Li et al., "Superparamagnetic Iron Oxide Nanoparticles as MRI contrast agents for Non-invasive Stem Cell Labeling and Tracking" Theranostics, Jul. 2013, 3(8):595-615, 21 pages.
Li et al., "Thiol-ene reaction: a versatile tool in site-specific labelling of proteins with chemically inert tags for paramagnetic NMR" Chemical Communications, Cambridge, United Kingdom, 48(21), 2704-2706, 2012, 18 pages.
Liu et al., "Photostimulated near-infrared persistent luminescence as a new optical read-out from Cr3+-doped LiGa5O8" Scientific Reports 3, Article 1554, Mar. 2013, 9 pages.
Lomstein and Jorgensen, "Pre-column liquid chromatographic determination of dipicolinic acid from bacterial endospores" Limnology and Oceanography: Methods, Apr. 2012, 10:4, 227-233, 14 pages.
Mahdavi et al., "Preparation, Characterization, and Application of Polyacrylamide-Polystyrene/Bentonite Nanocomposite as an Effective Immobilizing Adsorbent for Remediation of Soil" Chemistry Select, Apr. 5, 2020, 4538-4547, 12 pages.
Mahmoudi et al., "Superparamagnetic iron oxide nanoparticles development surface modification and applications in chemotherapy" Advanced Drug Delivery Reviews, Jan. 2011, 63, 24-46, 23 pages.
Manna et al., "Complexation behavior of trivalent actinides and lanthanides with 1,10-phenanthroline-2,9-dicarboxylic acid based ligands: insight from density functional theory" Physical Chemistry Chemical Physics, vol. 14, No. 31, Jan. 2012, 11060-11069, 10 pages.
Marais, A., et al. "Time-Resolved Fluorescence for Real-Time Monitoring of Both Scale and Corrosion Inhibitors: A Game-Changing Technique" SPE International Oilfield Scale Conference and Exhibition. OnePetro, May 2016, 11 pages.
Marchetti et al., "Fluorous affinity chromatography for enrichment and determination of perfluoroalkyl substances" Annual Review of Analytical Chemistry vol. 84, Jul. 19, 2012, 8 pages.
Martinez et al., "Polysaccharide-based Nanoparticles for Controlled Release Formulations" The Delivery of Nanoparticles, Published May 2012, 185-222, 40 pages.
Martini et al., "How to Monitor Scale Inhibitor Squeeze using Simple TRF Tracers" Society of Petroleum Engineers, presented at the SPE International Symposium on Oilfield Chemistry held in the Woodlands, Texas, Apr. 13-15, 2015, 8 pages.
Melton et al, "Complexes of Greatly Enhanced Thermodynamic Stability and Metal Ion Size-Based Selectivity, Formed by the Highly Preorganized Non-Macrocyclic Ligand 1,10-Phenanthroline-

(56) References Cited

OTHER PUBLICATIONS 2,9-dicarboxylic Acid: A Thermodynamic and Crystallographic Study" Inorganic Chemistry vol. 45 No. 23, Jun. 2006, 9 pages.

Moyner et al., "The Application of Flow Diagnostics for Reservoir Management" Society of Petroleum Engineers (SPE), Apr. 2015, 18 pages.

Muller and Seubert, "Ultra trace determination of fluorobenzoic acids in tap and reservoir water using solid-phase extraction and gas chromatography-mass spectrometry" Journal of Chromatography A, 1260, Oct. 2012, 7 pages.

Nie et al., "Probing Single Molecules and Single Nanoparticles by Surface-Enhanced Raman Scattering" Science, vol. 275, No. 5303, Feb. 1997, 1102-1106, 6 pages.

Ogden et al., "Complexation of Am(III) and Nd(in) by 1,10-Phenanthroli ne-2,9-Di carboxylic Acid" Journal of Solution Chemistry, vol. 42, No. 1, pp. 211-225, 2013, 15 pages.

Ouali et al., "Analysis of Paramagnetic NMR Spectra of Triple-Helical Lanthanide Complexes with 2,6-Dipicolinic Acid Revisited: A New Assignment of Structural Changes and Crystal-Field Effects 25 Years Later" Inorganic Chemistry, 41(6), Feb. 2002, 1436-1445, 10 pages.

Pallenberg et al. "Synthesis and Characterization of Some Copper(I) Phenanthroline Complexes" Inorg. Chem. 1995, 34, 2833-2840, 8 pages.

Park et al., "Application of montmorillonite in bentonite as a pharmaceutical excipient in drug delivery systems" Journal of Pharmaceutical Investigation, 46, May 2016, 363-375, 13 pages.

Parker and Williams, "Getting excited about lanthanide complexation chemistry" Journal of the Chemical Society, Dalton Transactions, vol. 18, 1996, 16 pages.

Parker et al., "Being excited by lanthanide coordination complexes: aqua species, chirality, excited-state chemistry, and exchange dynamics" Chemical Reviews, vol. 102, Issue 6, May 2002, 34 pages.

Petoud et al., "Brilliant SM, Eu, Tb, and Dy Chiral Lanthanide Complexes with Strong Circularly Polarized Luminescence" Journal fo the American Chemical Society (JACS), Dec. 15, 2006, 7 pages.

Potapov et al., "Nanometer-Scale Distance Measurements in Proteins Using Gd3+ Spin Labeling" Journal of the American Chemical Society, 132(26), Jun. 2010, 9040-9048, 9 pages.

Qianming et al., "Bspda Synthesis and its Europium (III) Complexes' Fluorescence" Chemical Industry Times, Jul. 2005, 19(7): 38-41, 4 pages (English Abstract).

Rashdan et al., "Effect of the preparation route, PEG and annealing on the phase stability of Fe3O4 nanoparticles and their magnetic properties" Journal of Experimental Nanoscience, vol. 8, No. 2, 2013, 210-222, 13 pages.

Rovani, "Enhanced Oil Recovery: Aqueous Flow Tracer Measurement" WRI-09-R002, OSTI.Gov, Technical Report, U.S. Department of Energy, Feb. 2009, 1-18, 25 pages.

Rowan et al., "Dynamic Covalent Chemistry" Angewante Chemie International Edition, Mar. 15, 2002, 55 pages.

Sabbatini et al., "Luminescent lanthanide complexes as photochemical supramolecular devices" Coordination Chemistry Reviews, vol. 123, issue 1-2, Feb. 1993, 28 pages.

Saeki et al., "Upper and lower critical solution temperatures in poly (ethylene glycol) solutions" Polymer, vol. 17, No. 8, Aug. 1976, 685-689, 5 pages.

Sammes and Yshioglu, "Modern bioassays using metal chelates as luminescent probes" Natural Product Reports, vol. 31, No. 1, 1996, 28 pages.

Sanni et al., "A field case study of inter-well chemical tracer test" in SPE International Symposium on Oilfield Chemistry, Society of Petroleum Engineers, Apr. 2015, 17 pages.

Sanni et al., "Pushing the envelope of residual oil measurement: A field case study of a new class of inter-well chemical tracers" Journal of Petroleum Science and Engineering, vol. 163, 2018, 19 pages.

Santarelli et al., "Formation Evaluation From Logging on Cuttings" SPE Reservoir Evaluation and Engineering, presented at the 1996 SPE Permian Basin Oil and Gas Recovery Conference, Mar. 27-29, 1996, published Jun. 1998, 7 pages.

Schmidt et al., "Copper dipicolinates as peptidomimetic ligands for the Src SH2 domain" Bioorganic & Medicinal Chemistry Letters, 14(16), 4203-4206, Aug. 2004, 4 pages.

Schmidt et al., "Synthesis of Mono- and Dinuclear Vanadium Complexes and Their Reactivity toward Dehydroperoxidation of Alkyl Hydroperoxides" Inorganic Chemistry 56(3), 2017, 1319-1332, 14 pages.

Selvin et al., "Principles and biophysical applications of lanthanide-based probes" Annual Review of Biophysics and Biomolecular Structure, Jun. 2002, 28 pages.

Serres-Piole et al., "Direct sensitive simultaneous determination of fluorinated benzoic acids in oil reservoir waters by ultra high-performance liquid chromatography-tandem mass spectrometry" Journal of Chromatography A, 1218, Aug. 2011, 6 pages.

Serres-Piole et al., "Water tracers in oilfield applications: Guidelines" Elsevier Ltd., Journal of Science and Engineering, Nov. 2012, 18 pages.

ShamsiJazeyi et al., "Polymer-Coated Nanoparticles for Enhance Oil Recovery" Journal of Applied Polymer Science, vol. 131, No. 15, Aug. 5, 2014, 13 pages.

Shook et al., "SPE 124614: Determining Reservoir Properties and Flood Performance from Tracer Test Analysis" Society of petroleum Engineers (SPE), presented at SPE Annual Technical Conference and Exhibition, Oct. 4-7, 2009, 19 pages.

Solomon et al., "Synthesis and Study of Silver Nanoparticles" Journal of Chemical Education vol. 84, No. 2, 2007, 332-325, 4 pages.

Song et al., "SERS-Encoded Nanogapped Plasmonic Nanoparticles: Growth of Metallic Nanoshell by Templating Redox-Active Polymer Brushes" Journal of the American Chemical Society (JACS), Apr. 28, 2014, 4 pages.

Stiles et al., "Surface-Enhanced Raman Spectroscopy" Annual Review of Analytical Chemistry, vol. 1, No. 1, Jul. 2008, 601-626, 29 pages.

Stryer et al., "Diffusion-enhanced fluorescence energy transfer" Annual Review of Biophysics and bioengineering, vol. 11, Issue 1, 1982, 21 pages.

Su et al., "A Dipicolinic Acid Tag for Rigid Lanthanide Tagging of Proteins and Paramagnetic NMR Spectroscopy" Journal of the American Chemical Society, 130(32), Jul. 2008, 10486-10487, 2 pages.

Tang et al., "Synthesis and fluorescence properties of Tb(III) complexes with pyridine-2,6-dicarboxylic acid derivatives" Journal of Central South University of Technology (English Edition), 15(5), Oct. 2008, 599-605, 7 pages.

Tang et al., "Synthesis of Novel Derivatives of Pyridine-2,6-dicarboxylic Acid" Synthetic Communications: An International Journal for Rapid Communication of Synthetic Organic Chemistry, 36(14), Jun. 2006, 2027-2034, 9 pages.

Tang et al., "Synthesis of Eu(III) and Tb(III) Complexes with Novel Pyridine-2,6-Dicarboxylic Acid Derivatives and Their Fluorescence Properties" Front. Chem. China, 2006, 4:, 408-413, 6 pages.

Thomas et al., "Deployment and Detection of a Novel Barcoded Advanced Tracers System for the Optimization of Improved Waterflood Recovery in Hydrocarbon Reservoirs" SPE-194872-MS, SPE Middle East Oil and Gas Show and Conference. Society of Petroleum Engineers, 2019, 10 pages.

Tian et al., "Off-Resonant Gold Superstructures as Ultrabright Minimally Invasive Surface-Enhanced Raman Scattering (SERS) Probes" American Chemical Society, Jul. 2015, 7 pages.

Toulhoat, "Experimentation and Modelling of U, Th and Lanthanides Transport in Fissured Rocks: Influence of Complexation" MRS Proceedings, vol. 50, Jan. 1, 1985, 8 pages.

Wahajuddin et al., "Superparamagnetic iron oxide nanoparticles: Magnetic nanoplatforms as drug carriers" International Journal of Nanomedicine, 7, Jul. 2012, 3445-3471, 27 pages.

Wang et al., "The Design and Implementation of a Full Field Inter-Well Tracer Program on a Giant UAE Carbonate Oil Field" in Abu Dhabi International Petroleum Exhibition and Conference, Society of Petroleum Engineers, SPE-177527-MS, Nov. 2015, 8 pages.

(56) References Cited

OTHER PUBLICATIONS

Wu et al., "A reusable biosensor chip for SERS-fluorescence dual mode immunoassay" Proc. SPIE 9543, Third International Symposium on Laser Interaction with Matter, 954317, May 4, 2015, 6 pages.

Wu et al., "A SERS-Assisted 3D Barcode Chip for High-Throughput Biosensing" Small Journal vol. 11, No. 23, Jun. 11, 2015, 9 pages.

Xu et al., "Superparamagnetic Photonic Crystals" Adv. Mater., Nov. 2001, 13, 1681-1683, 4 pages.

Xu et al., "Synthesis and Utilization of Monodisperse Superparamagnetic Colloidal Particles for Magnetically Controllable Photonic Crystals" Chem. Mater., 14(3), 2002, 1249-1256, 8 pages.

Xu et al., "Measurement of two-photon excitation cross sections of molecular fluorophores with data from 690 to 1050 nm" Journal of the Optical Society of America B, Mar. 1996, 11 pages.

Yang et al., "The Co-Luminescence Groups of Sm—La-pyridyl Carboxylic Acids and the Binding Characteristics between the Selected Doped Complex and Bovine Serum Albumin" Bulletin of the Korean Chemical Society 33(4), Apr. 20, 2012, 1303-1309, 7 pages.

Yang et al., "Paramagnetic labeling of proteins and pseudocontact shift in structural biology" Chinese Journal of Magnetic Resonance, 2014, 31(2):155-171, 12 pages (English Abstract).

Yu et al., "Adsorption of proteins and nucleic acids on clay minerals and their interactions: A review" Applied Clay Science, 80-81, Aug. 2013, 443-452, 10 pages.

Zamberi et al., "SPE 166005: Improved Reservoir Surveillance Through Injected Tracers In A Saudi Arabian Field: Case Study" Society of Petroleum Engineers (SPE), presented at SPE Reservoir Characterization and Simulation Conference and Exhibition, Sep. 2013, 15 pages.

Zemel, "Chapter 3: Interwell Water Tracers" Tracers in the Oil Field, vol. 43, 1st Edition, Elsevier Science, Jan. 13, 1995, 47 pages.

Zhang et al., "Water adsorption on kaolinite and illite after polyamine adsorption" Journal of Petroleum Science and Engineering, 142, Jun. 2016, 13-20, 8 pages.

Zhao et al., "Chromatographic Separation of Highly Soluble Diamond Nanoparticles Prepared by Polyglycerol Grafting" Angewandte Chemie International Edition, vol. 50, No. 6, Feb. 7, 2011, 1388-1392, 5 pages.

Zhou et al., "Upconversion luminescent materials: advances and applications" Chem Rev., Jan. 14, 2015, 71 pages.

Arora et al., "Hydrophobically modified sodium alginate conjugated plasmonic magnetic nanocomposites for drug delivery & magnetic resonance imaging," Materials Today Communications, Dec. 2020, 25(101470), 12 pages.

Iordache et al., "Magnetic chitosan grafted (alkyl acrylate) composite particles: Synthesis, characterization and evaluation as adsorbents," Arabian Journal of Chemistry, Dec. 29, 2015, 11:1032-1043, 12 pages.

Pandey et al., "On the Weak Intrinsic Luminescence from Paclitaxel Dissolved in Nonelectrolyte Solvents," Applied Spectroscopy, Aug. 1999, 53(8):991-999, 9 pages.

Rippe et al., "Synthesis and magnetic manipulation of hybrid nanobeads based on Fe3O4 nanoclusters and hyaluronic acid grafted with an ethylene glycol-based copolymer," Applied Surface Science, Apr. 30, 2020, 510(145354), 10 pages.

MULTIFUNCTIONAL MAGNETIC TAGS FOR MUD LOGGING

CROSS-REFERENCE TO RELATED PATENT APPLICATIONS

This application is a divisional of and claims the benefit of priority to U.S. patent application Ser. No. 17/454,176, filed Nov. 9, 2021, the contents of which are incorporated by reference herein.

TECHNICAL FIELD

This document relates to compositions and methods to determine an origin location of a subterranean cutting or sample.

BACKGROUND

Subterranean cuttings that are produced during drilling operations can provide critical information, for example, the lithology and mineral composition of the subterranean formation. However, cuttings produced at the drill head travel to the surface via the annulus, and it is difficult to accurately determine or even estimate lag time during this upward trip. This makes analyzing the depth at which these cutting originated difficult.

Mud tracers can be used to determine mud cycle time, for example, the circulation time, however, the estimating the depth of cuttings based on circulation time is inaccurate, especially if the wellbore includes long horizontal sections or the return trip time is lengthy. For example, when the return trip is longer than half an hour, it is common to have depth uncertainties of more than 6 meters (20 feet). This, in turn, compounds errors in characterizing the formation according to the depth of the cuttings. More efficient mud tracer materials and rapid detection techniques for these tracers are highly desirable.

SUMMARY

This disclosure describes compositions and methods that can be used to determine the origin depth of a wellbore cutting.

In some implementations, a nanoparticle tag includes a superparamagnetic iron oxide core, an intermediate layer comprising a fluorescent dye, and a polymer shell.

In some implementations, a method of making a nanoparticle tag includes providing a superparamagnetic iron oxide nanoparticle core, functionalizing the surface of the superparamagnetic iron oxide nanoparticle core to yield a functionalized nanoparticle core, and covalently bonding a fluorescent dye to the functionalized nanoparticle core.

In some implementations, a method of determining the origin location of a subterranean sample includes mixing a nanoparticle tag into a fluid, wherein the nanoparticle tag includes a superparamagnetic iron oxide core, an intermediate layer comprising a fluorescent dye, and a polymer shell. The method includes flowing the fluid through a work string into a subterranean formation, recovering subterranean samples from the subterranean formation, separating tagged samples from untagged samples using a magnet, and determining an origin location of the subterranean sample by analyzing the fluorescent signal of the nanoparticle tag.

The details of one or more implementations of the disclosure are set forth in the accompanying drawings and the description that follows. Other features, objects, and advantages of the disclosure will be apparent from the description and drawings, and from the claims.

DESCRIPTION OF DRAWINGS

Like reference symbols in the various drawings indicate like elements.

DETAILED DESCRIPTION

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Provided in this disclosure, in part, are tags, methods, and systems for tagging cuttings produced during a drilling operation. These tags, methods, and systems can be used to determine the origin location of a cutting or subterranean sample. The tags can absorb to, or decorate cuttings or subterranean samples. For example, the tags can have high affinity non-specific binding onto cuttings or subterranean samples as a result of physico-chemical and/or ionic forces, for example, Van der Waals, hydrophobic/hydrophilic interactions, and oppositely charged surfaces. The tags can be identified by multiple orthogonal techniques, and therefore the various combinations of orthogonally detectable features create a library of uniquely identifiable tags.

Figure 1:
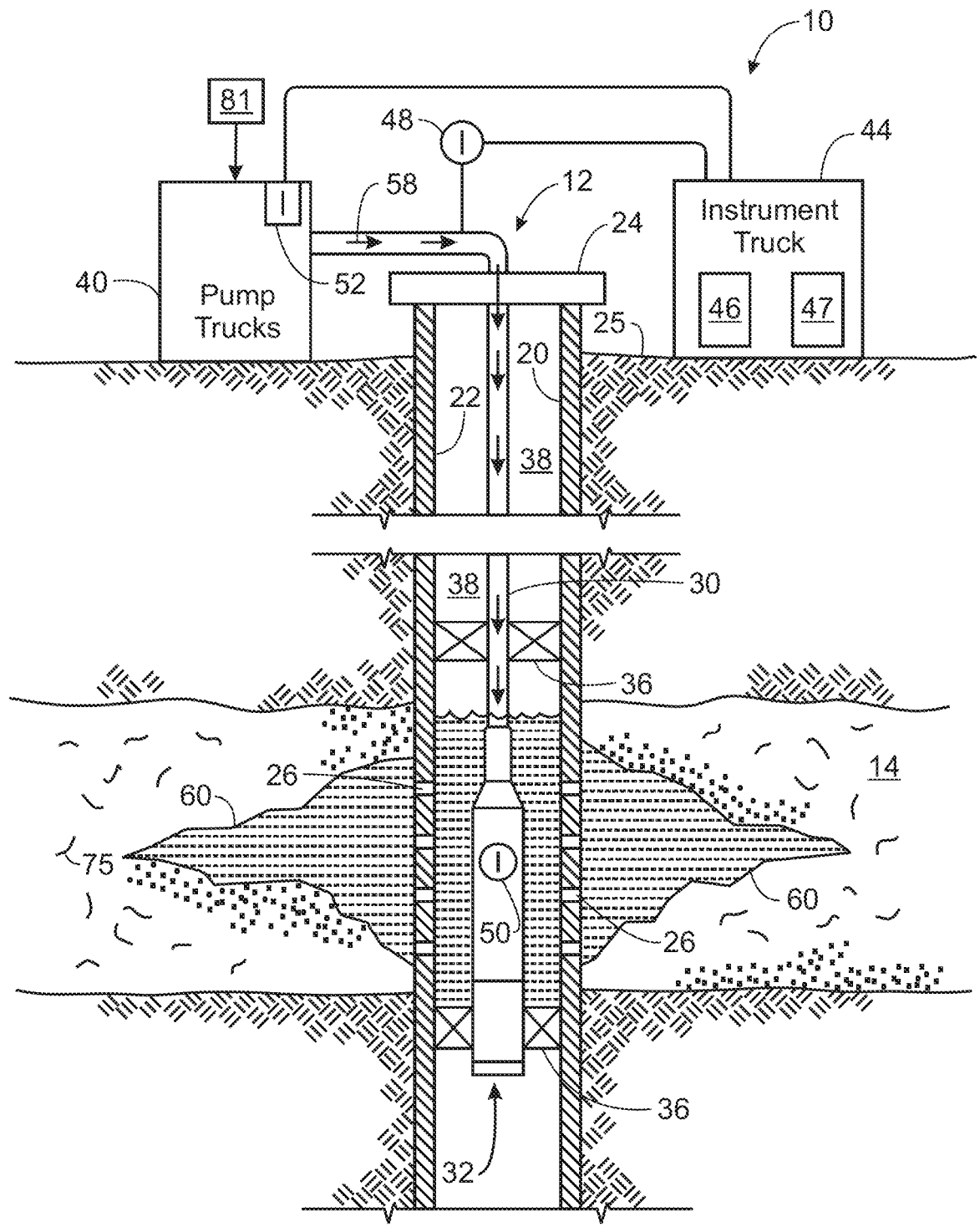
FIG. 1 shows an example schematic of a drilling operation 10 for a well 12.

FIG. 1 illustrates an example of a drilling operation 10 for a well 12. The well 12 can be in a wellbore 20 formed in a subterranean zone 14 of a geological formation in the Earth's crust. The subterranean zone 14 can include, for example, a formation, a portion of a formation, or multiple formations in a hydrocarbon-bearing reservoir from which recovery operations can be practiced to recover trapped hydrocarbons. Examples of unconventional reservoirs include tight-gas sands, gas and oil shales, coalbed methane, heavy oil and tar sands, gas-hydrate deposits, to name a few. In some implementations, the subterranean zone 14 includes an underground formation including natural fractures 60 in rock formations containing hydrocarbons (for example, oil, gas, or both). For example, the subterranean zone 14 can include a fractured shale. In some implementations, the well 12 can intersect other suitable types of formations, including reservoirs that are not naturally fractured in any significant amount.

The well 12 can include a casing 22 and well head 24. The wellbore 20 can be a vertical, horizontal, deviated, or multilateral bore. The casing 22 can be cemented or otherwise suitably secured in the wellbore 20. Perforations 26 can be formed in the casing 22 at the level of the subterranean zone 14 to allow oil, gas, and by-products to flow into the well 12 and be produced to the surface 25. Perforations 26 can be formed using shape charges, a perforating gun, or otherwise.

For a drilling treatment 10, a work string 30 can be disposed in the wellbore 20. The work string 30 can be coiled tubing, sectioned pipe, or other suitable tubing. A drilling tool or drill bit 32 can be coupled to an end of the work string 30. Packers 36 can seal an annulus 38 of the wellbore 20 uphole of and downhole of the subterranean zone 14. Packers 36 can be mechanical, fluid inflatable, or other suitable packers.

One or more pump trucks 40 can be coupled to the work string 30 at the surface 25. The pump trucks 40 pump drilling mud 58 down the work string 30 to lubricate and cool the drilling tool or drill bit 32, maintain hydrostatic pressure in the wellbore, and carry subterranean cuttings to the surface. The drilling mud 58 can include a fluid pad, proppants, flush fluid, or a combination of these components. The pump trucks 40 can include mobile vehicles, equipment such as skids, or other suitable structures.

One or more instrument trucks 44 can also be provided at the surface 25. The instrument truck 44 can include a drilling control system 46 and a drilling simulator 47. The drilling control system 46 monitors and controls the drilling treatment 10. The drilling control system 46 can control the pump trucks 40 and fluid valves to stop and start the drilling treatment 10. The drilling control system 46 communicates with surface and subsurface instruments to monitor and control the drilling treatment 10. In some implementations, the surface and subsurface instruments may comprise surface sensors 48, down-hole sensors 50, and pump controls 52.

Additives 81 can be mixed with drilling mud 58 and flowed through the reservoir. In some implementations, the additives are tags that can embed into or decorate the surface of cuttings produced by the drill bit. When drilling mud is introduced into the subterranean formation via the drill bit, tags that are included in the mud will contact the subterranean formation for the first time at the drill head. If the depth or relative position of the drill head and the lag time of the mud in the drill string are known, cuttings that are tagged with a specific tag can be accurately assigned an origin depth or position. Accordingly, the origin location of the cutting can be accurately determined.

In some implementations, more than one tag can be used. The tags can be uniquely identifiable. Accordingly, cuttings that include or are decorated with a first tag can be assigned to a first depth or position, and cuttings that include or are decorated with a second tag can be assigned to a second depth or position. The number of tags is not limited to two, and the tags can uniquely identify a third, fourth, fifth, etc. depth or position.

Figure 2:
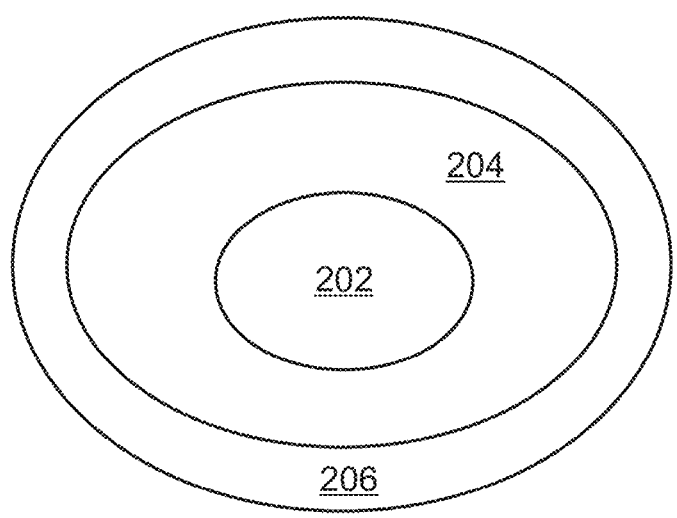
FIG. 2 shows an example of a magnetic nanoparticle tag.

The tags described herein are magnetic nanoparticle tags (MNPs) that can be used to tag subterranean cuttings or samples. FIG. 2 shows an example of a magnetic nanoparticle tag 200. The tag includes a magnetic core 202, a fluorescent dye intermediate layer 204, and a polymer shell 206. The magnetic core can be either a single superparamagnetic nanoparticle or a cluster of aggregated superparamagnetic nanoparticles. The magnetic core allows samples tagged with the magnetic nanoparticle tags to be separated and collected by a magnetic field. The fluorescent dye can yield a fluorescent signal. The fluorescent signal can be detected and used to identify the magnetic tag. Further, the polymer shell 206 can be analyzed with mass spectrometry to produce a unique signal based on its constituent monomers. The polymer shell can be either a continuous coating layer or discrete patch decoration on the fluorescent magnetic cores. Unique combinations of fluorescence and mass spectrometry signals can be used to create a library of uniquely identifiable magnetic nanoparticle tags. Advantageously, all of the components of the MNPs are inexpensive and non-toxic. Therefore, these tags can be readily used in large quantities and in subterranean applications.

The tags are synthesized with covalent and/or physicochemical bonding between the magnetic core, dye molecules, and polymer. The resulting composite nanoparticles are chemically stable in an aqueous environment. Accordingly, the tags are suitable for use in oil-based or water-based drilling muds and subterranean applications.

The magnetic core 202 can include inorganic iron oxides, for example magnetite $Fe_3O_4$, maghemite gamma-$Fe_2O_3$, cobalt ferrite $CoFe_2O_4$, nickel ferrite $NiFe_2O_4$, or manganese ferrite $MnFe_2O_4$. The size of the primary nanoparticles of iron oxide are controlled to be less than 15 nm, so that a single or cluster of iron oxide nanoparticles are superparamagnetic. Superparamagnetism is a form of magnetism that appears in small ferromagnetic or ferrimagnetic nanoparticles. In sufficiently small nanoparticles, magnetization can randomly flip direction under the influence of temperature, and thus their magnetization appears to be in average zero, i.e., in the superparamagnetic state. In this state, an external magnetic field is able to magnetize the nanoparticles, similarly to a paramagnet. Superparamagnetic iron oxide particles (SPIONs) can be magnetized by an external magnetic field, however, SPIONs do not show magnetic interactions after the external magnetic field is removed. Accordingly, tags that include a superparamagnetic core can be separated, collected, and preconcentrated by an applied magnetic field, for example by using a magnet. In some implementations, the magnetic properties of the core can be used to separate unbound tags from drilling mud. Accordingly, these tags can be removed from the mud and the mud can be used again, either without tags or with a new tag. This prevents residual tags from contributing to background signals or interfering with subsequent drilling operations.

The magnetic core 202 can be synthesized by a precipitation reaction of $Fe^{3+}$ and $Fe^{2+}$ ions at a 2:1 molar ratio in a basic solution at room temperature. The basic solution can include NaOH or $NH_3 \cdot H_2O$ in solution. Equation 1 shows the precipitation of these ions to iron oxide $Fe_3O_4$. The superparamagnetic $Fe_3O_4$ nanoparticles as the magnetic cores in these syntheses. In the presence of oxygen, the precipitated $Fe_3O_4$ can slowly react with $O_2$ to yield gamma-$Fe_2O_3$, as shown by the Equation 2. The resulting gamma-$Fe_2O_3$ nanoparticles are also superparamagnetic, and therefore does not interfere in the function of the resulting nanoparticle.

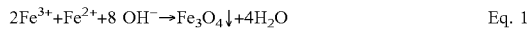

$$2Fe^{3+} + Fe^{2+} + 8\ OH^- \rightarrow Fe_3O_4 \downarrow + 4H_2O \qquad \text{Eq. 1}$$

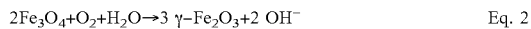

$$2Fe_3O_4 + O_2 + H_2O \rightarrow 3\ \gamma\text{-}Fe_2O_3 + 2\ OH^- \qquad \text{Eq. 2}$$

In some implementations, the surfaces of the iron oxide nanoparticles are functionalized by silane coupling agents. The silane coupling agents can contain different functional groups. For example, polyethylenimine (PEI) groups can be grafted onto the hydroxyl groups on the iron oxide surfaces through a hydrolysis reaction of trimethoxysilylpropyl modified polyethylenimine (silane-PEI). In some implementations, the PEI group is a linear polyethylenimine that contains secondary amines. In some implementations, the PEI group is a branched PEI group that contains primary, secondary, and tertiary amino groups.

Figure 3:
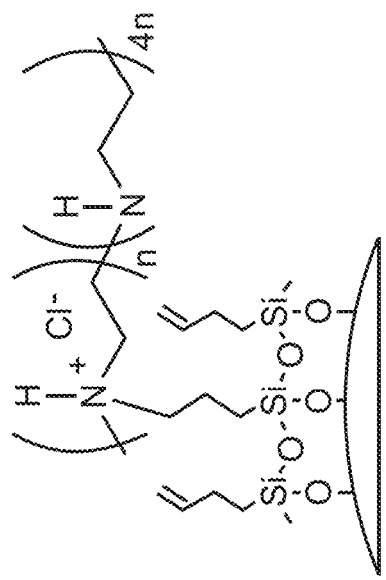
FIG. 3 shows an example reaction of an $Fe_3O_4$ nanoparticle (NP) surface, trimethoxysilylpropyl modified polyethylenimine (silane-PEI), and allyltrimethoxysilane (ATMOS).
Figure 3:
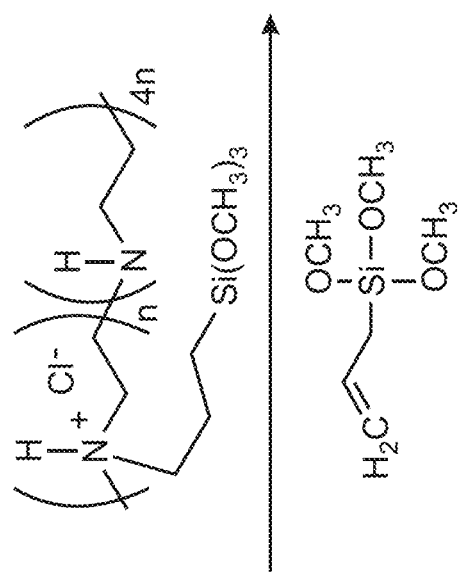
Figure 3:
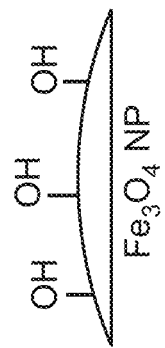
Figure 4:
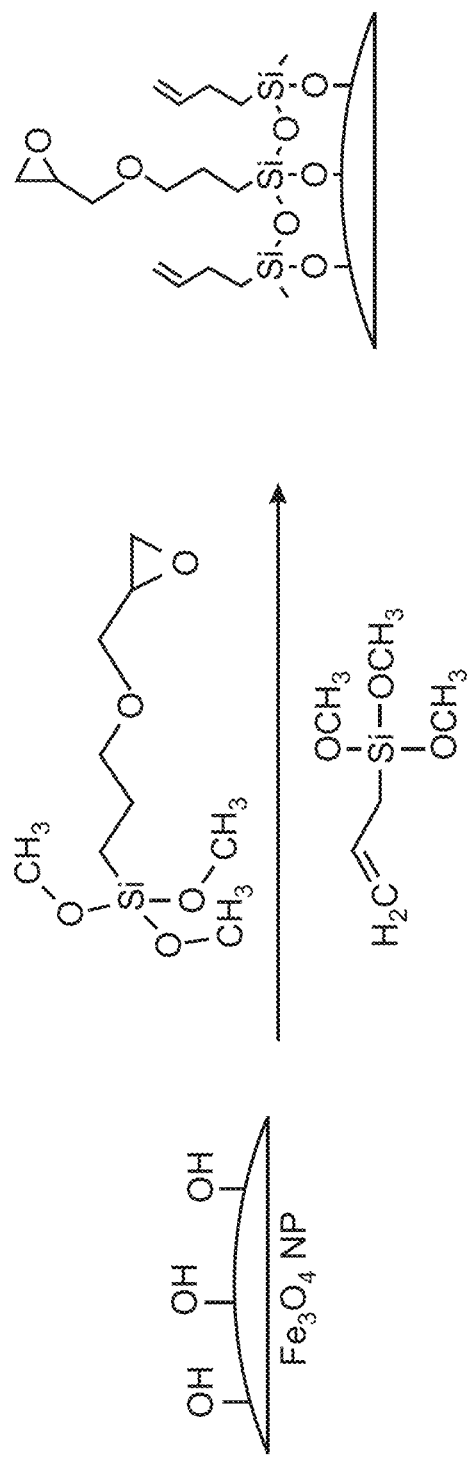
FIG. 4 shows an example reaction of an $Fe_3O_4$ nanoparticle (NP) surface, 3-glycidoxypropyltrimethoxysilane (GPTMS), and allyltrimethoxysilane (ATMOS).

In another example, allyl groups can be bound to the surface of the iron oxide nanoparticle by a reaction between the hydroxyl groups on the iron oxide surface and allyltrimethoxysilane (ATMOS) or 3-(trimethoxysilyl)propyl methacrylate (TMSPMA). FIG. 3 shows an example reaction of an $Fe_3O_4$ nanoparticle (NP) surface, silane-PEI with n and 4n repeating units giving a molecular weight 1500-1800 g/mol, and ATMOS to yield a functionalized nanoparticle. In this example, the functionalized nanoparticle contains PEI functional groups as well as allyl functional groups. FIG. 4 shows an example reaction of an $Fe_3O_4$ nanoparticle (NP) surface, 3-glycidoxypropyltrimethoxysilane (GPTMS), and ATMOS to yield a functionalized nanoparticle. In this example, the functionalized nanoparticle contains PEI function groups as well as epoxy functional groups. FIGS. 3-4 illustrate reactions with an $Fe_3O_4$ iron oxide core, however, it is understood that these reactions can also occur on the surface of a $\gamma\text{-}Fe_2O_3$ nanoparticle, a $CoFe_2O_4$ nanoparticle, a $NiFe_2O_4$ nanoparticle, or a $MnFe_2O_4$ nanoparticle. Therefore, the functionalized nanoparticle can contain either an $Fe_3O_4$, a $\gamma\text{-}Fe_2O_3$, a $CoFe_2O_4$, a $NiFe_2O_4$, or a $MnFe_2O_4$ core. Further, the functionalized nanoparticle can be functionalized with a single functional group or with any combination of the functional groups described herein. For example, the functionalized nanoparticle can contain only PEI, epoxy, or allyl, or any combination of these groups. In some implementations, the functional groups on the functionalized nanoparticles are used to incorporate fluorescent dyes to yield the fluorescent dye layer.

The fluorescent dye layer 204 can include fluorescent dyes, for example fluorescein isothiocyanate (FITC), tetramethylrhodamine isothiocyanate (TRITC), and Rhodamine B isothiocyanate (RBITC). Other suitable dyes include Rhodamine 123, Congo Red, Evans Blue, and NIR-797, etc. The individual fluorescent dyes have unique fluorescence properties, i.e., different emission spectra under different excitation wavelengths. Therefore, in addition to being detectable by fluorescence imaging or spectroscopic methods, the fluorescent dyes can be used to differentiate unique tags from one another.

Figure 5:
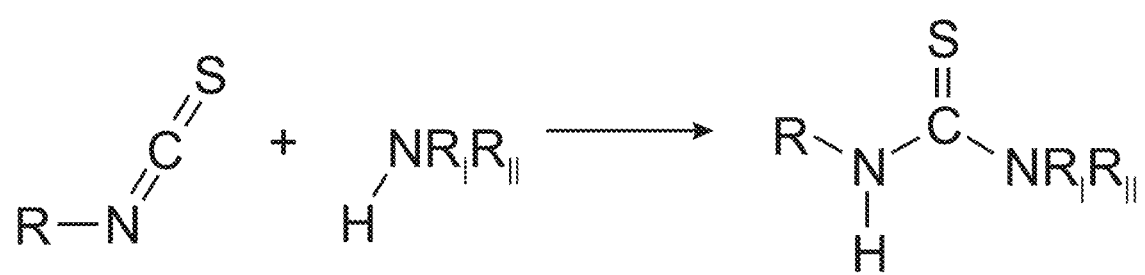
FIG. 5 shows an example reaction between an amine and an isothiocyanate to yield a thiourea.
Figure 6:
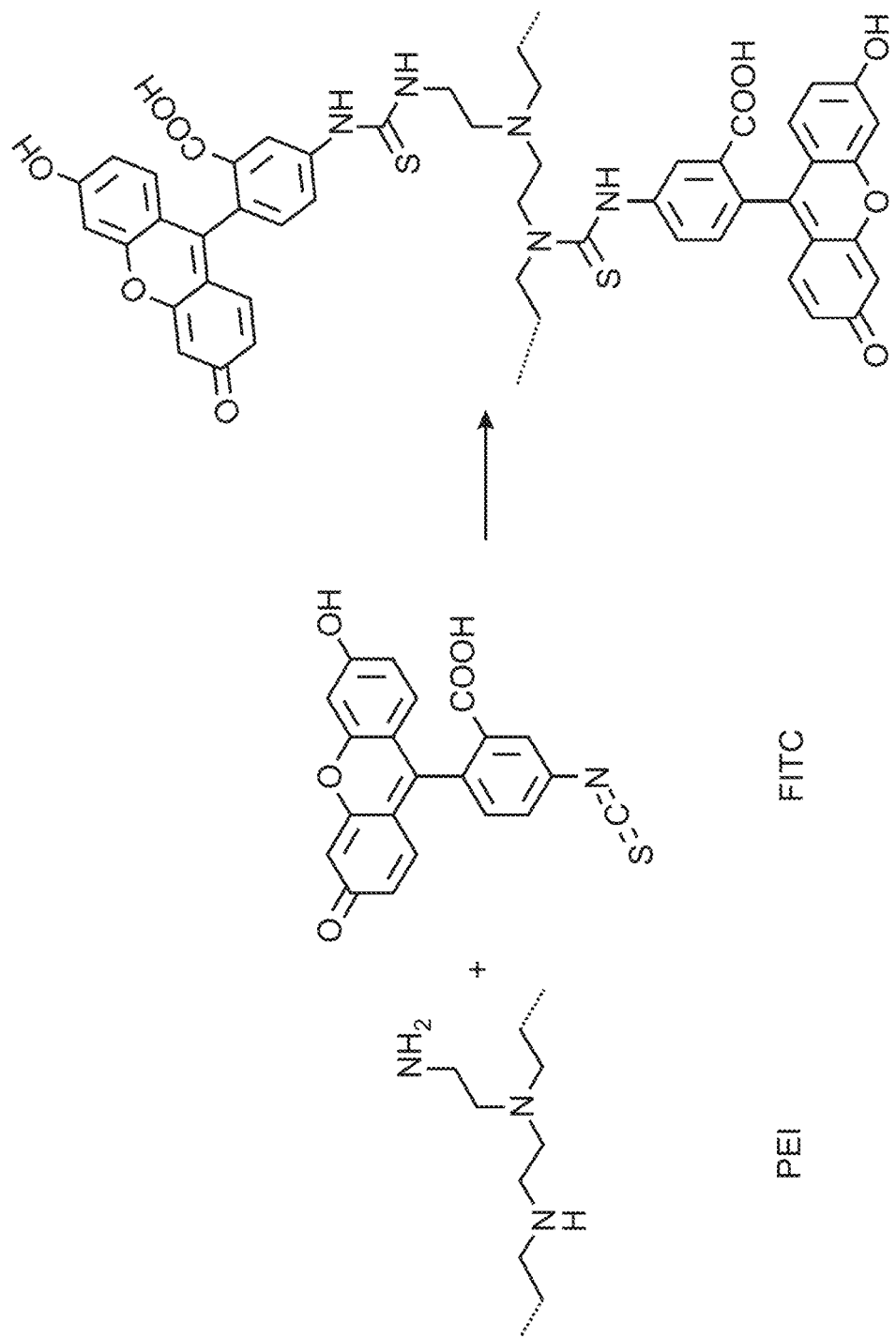
FIG. 6 shows an example reaction of a PEI group and the isothiocyanate-containing dye FITC.

In some implementations, the fluorescent dyes are covalently bonded to a functionalized iron oxide nanoparticle by a reaction between a PEI group and an isothiocyanate-containing dye. The PEI group can contain primary, secondary, or tertiary amines. Isothiocyanate groups will react with primary and secondary amines to yield substituted thioureas. FIG. 5 shows a general reaction between an amine and an isothiocyanate to yield a thiourea. The functional groups RI and Ru can be H, alkyl, or aryl groups. Accordingly, fluorescent dye molecules that contain isothiocyanate can be covalently bonded to a functionalized nanoparticle that contains PEI groups. Suitable isothiocyanate-containing fluorescent dyes include fluorescein isothiocyanate (FITC), Rhodamine B isothiocyanate (RBITC), tetramethylrhodamine isothiocyanate (TRITC), and NIR-797 isothiocyanate. These dyes have demonstrated stability at subterranean and reservoir conditions, such as high temperatures and pressures, at least for several days. Accordingly, these dyes are suitable for use in drilling and wellbore operations. FIG. 6 shows an example reaction of a PEI group and the isothiocyanate-containing dye FITC.

Figure 7:
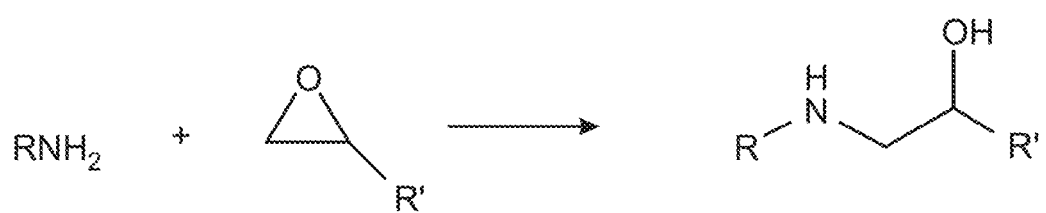
FIG. 7 shows an example reaction between a primary amine and an epoxy.
Figure 8:
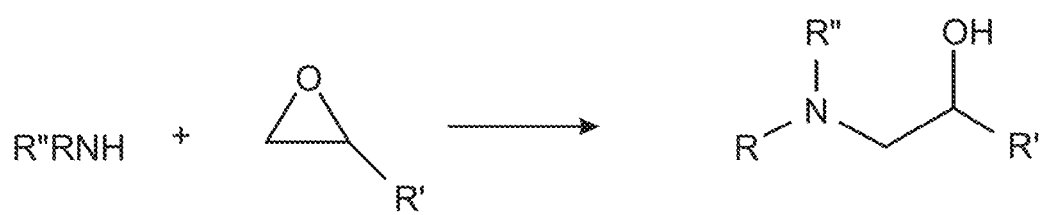
FIG. 8 shows an example reaction between a secondary amine and an epoxy resin.
Figure 9:
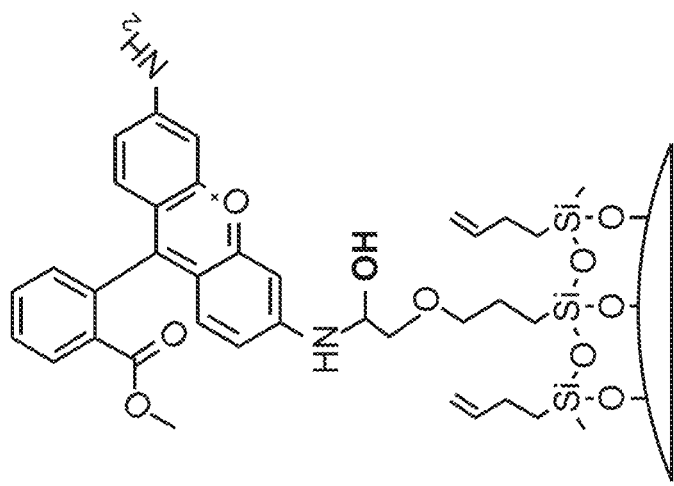
FIG. 9 shows an example of an amine-containing dye, Rhodamine 123, binding to an epoxy-containing functionalized nanoparticle.
Figure 9:
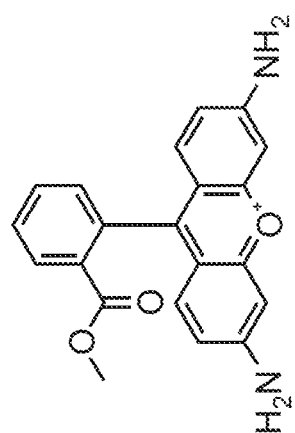
Figure 9:
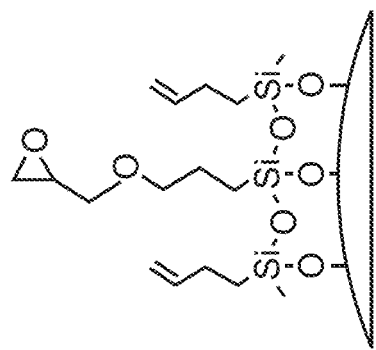

In some implementations, a fluorescent dye can be covalently bound to a functionalized nanoparticle that contains epoxy groups. For example, the reaction between an epoxy and an amine functional group yields a cured epoxy resin. FIG. 7 shows the general reaction between a primary amine and an epoxy. FIG. 8 shows the general reaction between a secondary amine and an epoxy resin. For nanoparticles that are functionalized to include epoxy groups, dye molecules with amine groups can covalently bind to the nanoparticles. For example, Rhodamine 123, Congo Red, and Evans Blue containing amino group can react with functionalized nanoparticles that contain epoxy groups. FIG. 9 shows an example of an amine-containing dye, Rhodamine 123, binding to an epoxy-containing functionalized nanoparticle.

Each of the fluorescent dyes described herein have a unique emission spectrum under different excitation wavelengths. Therefore, each of these dyes, and the tags that incorporate these dyes, can be uniquely identified by fluorescence analysis. Table 1 lists the excitation and emission wavelengths of the dyes described herein.

TABLE 1

Maximum Excitation and Emission Wavelengths of Fluorescent Dyes

| Dye | Excitation Wavelength (nm) | Emission Wavelength (nm) |
| --- | --- | --- |
| FITC | 495 | 519 |
| Rhodamine 123 | 507 | 529 |
| TRITC | 544 | 570 |
| RBITC | 570 | 595 |
| Congo Red | 497 | 614 |
| Evans Blue | 540 | 680 |
| NIR-797 | 795 | 817 |

In some implementations, the tags described herein can include a polymer shell. The polymer shell 206 can include a polymer that contains styrene-based, methacrylate-based, or amine-based monomers. This polymer can be a thermally depolymerizable or degradable polymer. Accordingly, the polymer can be decomposed into its constituent monomers, for example by pyrolysis-gas chromatography-mass spectrometry (pyrolysis-GC-MS). Polymers that contain unique monomers and/or unique amounts of monomers can be "fingerprinted" by pyrolysis-GC-MS analysis. In other words, tags with unique combinations of monomers can be differentiated from one another using mass spectrometry. Suitable monomers include styrene, p-methylstyrene, p-methoxystyrene, 2,4-dimethyl styrene, 2,4,6-trimethyl styrene, 4-chlorostyrene, 3-chlorostyrene, 2-chlorostyrene, 4-bromostyrene, 3-bromo styrene, 2-bromostyrene, 4-fluorostyrene, 3-fluorostyrene, 2-fluorostyrene, 4(trifluoromethyl)styrene, 3-(trifluoromethyl)styrene, 2-(trifluoromethyl) styrene, 2,3,4,5,6-pentafluorostyrene, allylbenzene, allylpentafluorobenzene, phenyl methacrylate, hexyl methacrylate, butyl methacrylate, isobutyl methacrylate, propyl methacrylate, vinyl methacrylate, methyl methacrylate, 2-hydroxyethyl methacrylate, pentafluorophenyl methacrylate, allylamine, 3-buten-1-amine, N-allylmethylamine, allylmethylamine, N-vinylformamide, 2-methyl-2-propen-1-amine, and 2-methylallylamine.

In a general procedure for the polymer coating, 100 mL of fluorescence dye-labeled $Fe_3O_4$ nanoparticle suspension at 1-5 wt % in DI water in a round-bottom flask was degassed with $N_2$ for 15 min, and then 2.5 g sodium dodecyl sulfate (SDS) was dissolved in the DI water. Next, 0.2 g of potassium persulfate ($K_2S_2O_8$) was added with stirring under an $N_2$ purge. After dissolution of the $K_2S_2O_8$ initiator and the solution was heated to 90° C., 1-5 mL of styrenic monomer was injected at 0.02 mL/min by a syringe using a programmable syringe pump. After addition of the monomer, the reaction was allowed to proceed for 30 min and the reaction was then cooled to room temperature. The weight ratio of nanoparticle core and polymer shell in the synthesized composite particles can be adjusted by relative concentration of the nanoparticle suspension and monomer solution.

In some implementations, allyl groups that are present in the functionalized iron oxide nanoparticles can be used to react with polymers to create the polymer coating. These allyl groups can react with monomers during radical induced polymerization by persulfate ions, which chemically anchors the polymer layer onto the nanoparticles. Free-radical polymerization is a type of chain-growth polymerization in polymer synthesis.

The fluorescent dyes and polymer shells describe in this application can be used in any combination to result in a library of uniquely identifiable tags. These tags can be used as mud logging tracers. For example, the tags can be mixed with the drilling mud and flowed or pumped down a work string into a subterranean formation. The mud and tag mixture exits the work string at the drill bit. Accordingly, the tags come into contact with the subterranean formation for the first time as they exit the drill bit. The tags can bind onto surface of reservoir rocks through physical adsorption as a result of physico-chemical and/or ionic forces, for example, Van der Waal s, hydrophobic/hydrophilic interactions, and oppositely charged surfaces. Thus the tags can embed into or decorate the subterranean formation and the cuttings produced by the drill. The drilling mud carries the cuttings with the tags to the surface of the wellbore, where they can be recovered and analyzed. In some implementations, the cuttings recovered at the surface are cursorily washed with water before subsequent separation and analysis to remove any unbound tags on the cutting surface.

In some implementations, the tagged cuttings or samples are separated from the untagged samples using a magnet. Advantageously, this also pre-concentrates the tagged samples, and reduces the number of samples that need to be subsequently analyzed. The identity of the tags can be determined by a number of techniques, including fluorescent analysis and mass spectrometry. Fluorescent analysis can be used to determine the identity of the fluorescent dye present in the tag. Typical fluorescence analysis includes fluorescence imaging or fluorescence spectroscopy. The fluorescence images can be taken by a camera system or fluorescence microscopy under UV or visible light excitation, while the fluorescence spectra can be recorded by a portable spectroscopic system on site. In some implementations, the fluorescent analysis can occur at the wellbore or drilling site. The fluorescent analysis can provide a first set of real-time data about the tags and cuttings. This data can be used to make subsequent decisions about drilling operations. Alternatively or in combination, the tags can be analyzed with mass spectrometry, for example pyrolysis-gas chromatography-mass spectrometry, as described herein. In some implementations, the mass spectrometry analysis can be done at the wellbore or drilling site. In other implementations, the mass spectrometry analysis occurs off-site, for example in a laboratory.

The tags described herein can be engineered with unique fluorescence and mass spectrometry signals, as described in detail above. Accordingly, different combinations of different fluorescence and mass spectrometry signals can create a library of uniquely identifiable tags. In some implementations, a first tag can be introduced to a subterranean formation at a first time point, and a second tag can be introduced to a subterranean formation at a second time point. Therefore, when the position of the drill bit and the lag time of the tags as they travel through the work string is known, cuttings or subterranean samples tagged with a first tag can be assigned a first origin location, and subterranean samples tagged with a second tag can be assigned to a second origin location. The number of tags is not limited to two, and a plurality of tags can be used to assign a plurality of origin locations. Further, unbound tags can be separated from drilling mud using a magnet. Accordingly, the mud can be recycled and reused for subsequent tags, without background interference from previous tags.

Figure 10:
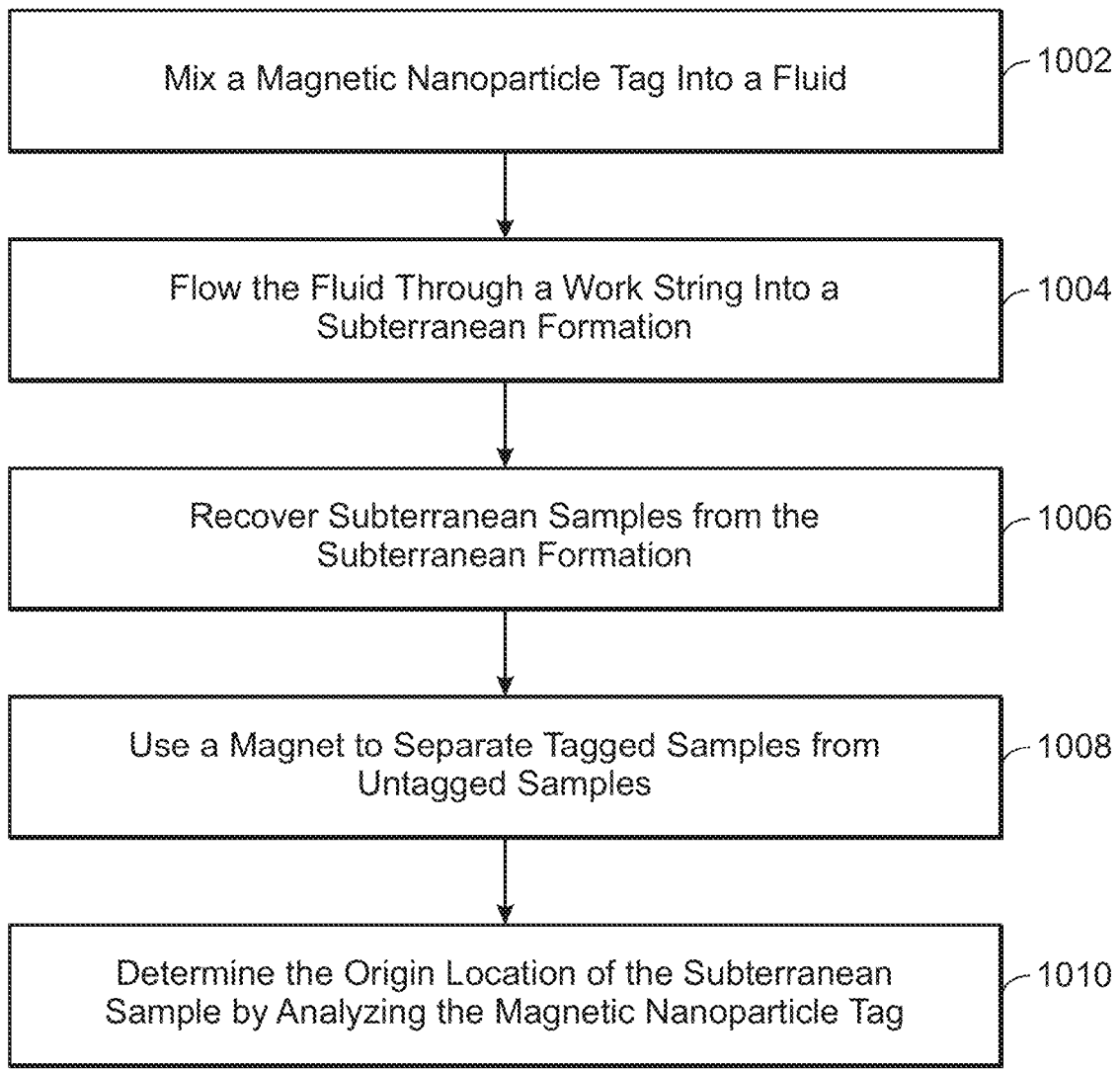
FIG. 10 shows a flowchart of an example method of determining the origin location of a subterranean cutting produced during drilling.

FIG. 10 shows a flowchart of an example method 1000 of determining the origin location of a subterranean cutting produced during drilling. At 1002, a magnetic nanoparticle tag is mixed into a fluid. At 1004, the fluid is flowed through a work string into a subterranean formation. At 1006, subterranean samples are recovered from the subterranean formation. At 1008, a magnet is used to separate tagged samples from untagged samples. At 1010, the origin location of the subterranean sample is determined by analyzing the magnetic nanoparticle tag.

EXAMPLE 1: SYNTHESIS OF $Fe_3O_4$ NANOPARTICLES

Figure 11:
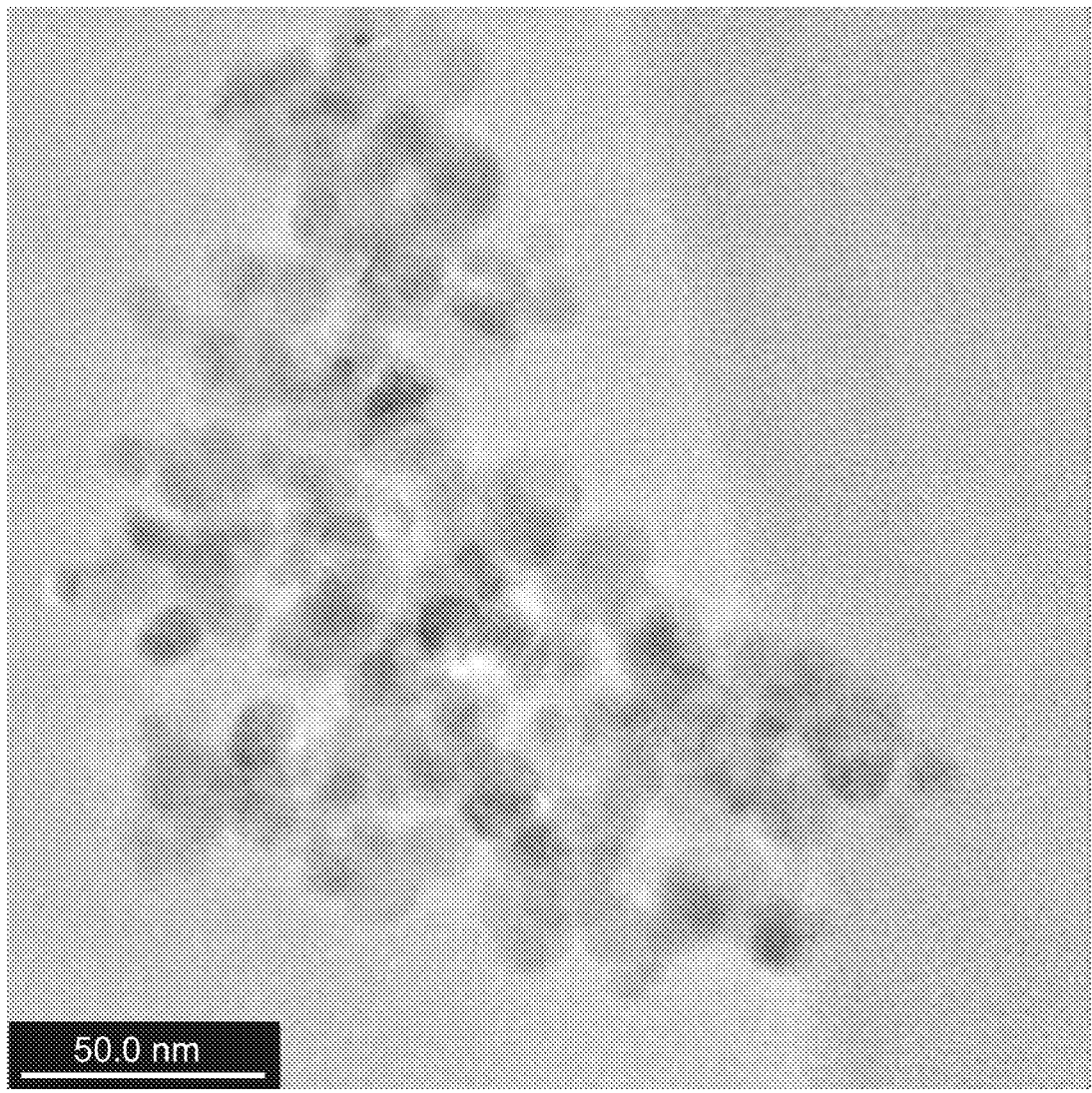
FIG. 11 shows an example TEM image of synthesized $Fe_3O_4$ nanoparticles.

A 500 mL solution of 0.1 M $Fe^{3+}$ and 0.05 M $Fe^{2+}$ was prepared by dissolving 27.0 g $FeCl_3 \cdot 6H_2P$ and 13.9 g $FeSO_4 \cdot 7H_2O$ in deionized (DI) water in a conical flask, then 25 mL of 29.5 wt % ammonia solution was added dropwise at a rate of 2.5 mL/min into the solution under vigorous stirring. With the addition of ammonia solution, iron hydroxide nanoparticles formed immediately, and the solution turns to black and viscous and then to deep brown and becomes more fluid. The formed colloidal suspension was continuously stirred for >12 hours at room temperature, which ages iron hydroxide to iron oxide in water suspension. According to the stoichiometric ratio, nominal 5.84 g $Fe_3O_4$ was produced in the batch of synthesis. FIG. 11 shows an example TEM image of synthesized $Fe_3O_4$ nanoparticles.

EXAMPLE 2: SURFACE FUNCTIONALIZATION OF $Fe_3O_4$ IRON OXIDE NANOPARTICLES WITH FITC

In a typical functionalization of the synthesized $Fe_3O_4$ NPs, a mixture of silane agents, 1 g trimethoxysilylpropyl modified polyethylenimine (Silane-PEI) and 0.25 g allyltrimethoxysilane (ATMS) in 25 mL ethanol, were added to the above iron oxide suspension, and the reaction was allowed to complete under stirring for another 12 hours. The functionalized $Fe_3O_4$ NPs were collected by a magnet and redispersed in 500 mL water. To label the magnetic NPs by fluorescent dye, 0.05 g FITC in 25 mL water, was added to the functionalized $Fe_3O_4$ suspension and stirring for 6 hours, allowing the dye molecules covalently bonding to amine groups.

EXAMPLE 3: POLYSTYRENE COATING OF FITC-FUNCTIONALIZED $Fe_3O_4$ NANOPARTICLES

To coat the magnetic FITC labeled $Fe_3O_4$ NPs with a polymer, 2 mL of tetramethylammonium hydroxide (TMAOH) was added to the $Fe_3O_4$ suspension under mechanical stirring. After 15 min of deoxygenating with $N_2$ bubbling, 6.0 mL styrene was added into the reaction mixture. The reaction mixture was heated to 75° C. and 1.0 g ammonium persulfate was added to initiate polymerization, which reacted for 2 h. The resulting polystyrene (PS) coated magnetic fluorescent NPs were harvested by a magnet. With this example synthesis procedure, the weight ratio of magnetic NP to the polymer is about 1:1 in the resulting composite particles. Depending on the amount of monomer used during the coating process, the weight ratio of magnetic NP to the polymer can be tuned from 9:1 to 1:9.

Figure 12:
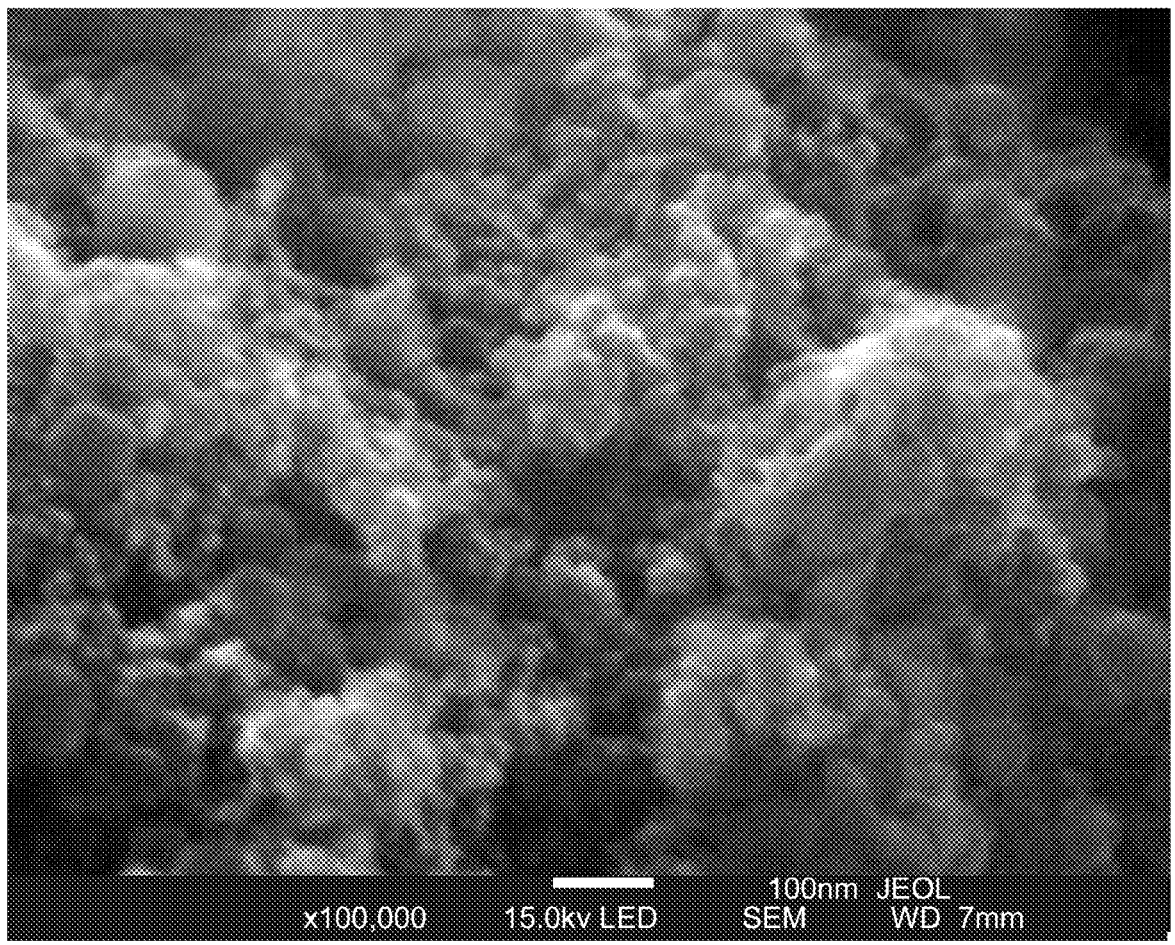
FIG. 12 shows an example SEM image of polystyrene coated, functionalized nanoparticles.

FIG. 12 shows an example SEM image of polystyrene coated, functionalized nanoparticles.

EXAMPLE 4: FLUORESCENCE ANALYSIS OF FITC-FUNCTIONALIZED $Fe_3O_4$ COATED NANOPARTICLES

Figure 13:
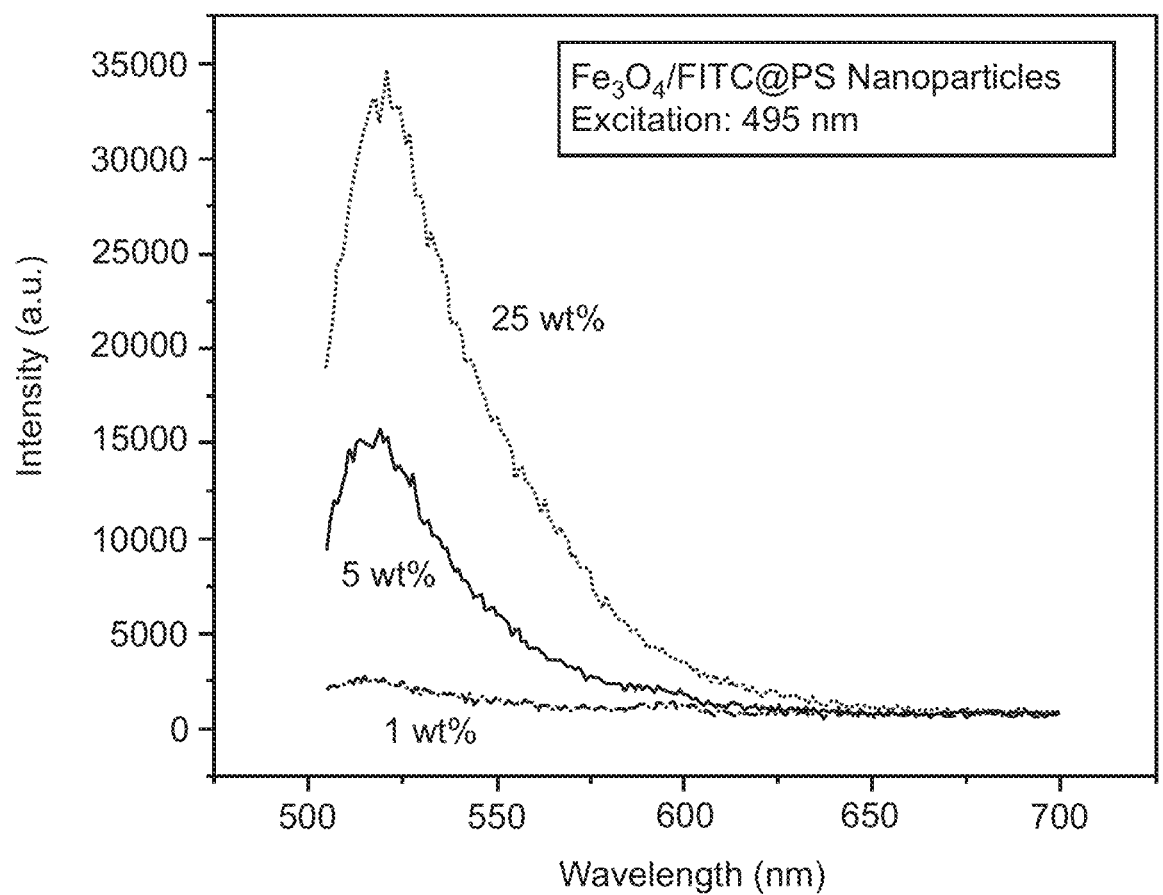
FIG. 13 shows an example fluorescence analysis of FITC-functionalized $Fe_3O_4$ nanoparticles coated in polystyrene at an excitation wavelength of 495 nm.

FIG. 13 shows an example fluorescence analysis of FITC-functionalized $Fe_3O_4$ nanoparticles coated in polystyrene at an excitation wavelength of 495 nm. These functionalized, coated nanoparticles were analyzed at a concentration of 1 wt %, 5 wt % and 25 wt % in mud. A tagged mud was prepared by mixing the synthesized FITC-$Fe_3O_4$-PS nanoparticles and clay powder (bentonite) at 1:99, 5:95 and 25:75 weight ratios, and then 1 g of the mixture was mixed with 10 mL water. The slurry with fluorescent magnetic tags was applied to wet the core when cutting a core of dolomite rock (diameter 3.8 cm) by a Buehler Isomet low speed saw. A piece of the sliced rock was collected and sonicated in 5 mL of water, and then the water suspension was transferred to a quartz cell. For the fluorescence measurement, a neodymium magnet was placed against a wall of the quartz cell to collect the magnet tagged particles for 10 mins, and then the spectra were recorded on the collected particles by a Horiba NanoLog-3 fluorescence spectrometer in a front face reflectance mode at excitation wavelength of 495 nm.

EXAMPLE 5: SURFACE FUNCTIONALIZATION OF $Fe_3O_4$ IRON OXIDE NANOPARTICLES WITH RBITC

To functionalize the surface of the synthesized $Fe_3O_4$ NPs, a mixture of silane agents, 1 g trimethoxysilylpropyl modified polyethylenimine (Silane-PEI) and 0.25 g allyltrimethoxysilane (ATMS) in 25 mL ethanol, was added to the iron oxide suspension as described in Example 1, and the reaction was allowed to complete under stirring for another 12 hours. The functionalized $Fe_3O_4$ NPs were collected by a magnet and redispersed in 500 mL water. To label the magnetic NPs with the dye RBITC, 0.05 g RBITC in 25 mL water was added to the functionalized $Fe_3O_4$ suspension and stirred for 6 hours, allowing the dye molecules to covalently bond to amine groups.

EXAMPLE 6: POLYSTYRENE COATING OF RBITC-FUNCTIONALIZED $Fe_3O_4$ Nanoparticles To coat the magnetic RBITC labeled $Fe_3O_4$ NPs with a polymer, 2 mL of tetramethylammonium hydroxide (TMAOH) was added to the $Fe_3O_4$ suspension under mechanical stirring. After 15 min of deoxygenating with $N_2$ bubbling, 6.0 mL methyl methacrylate was added into the reaction mixture. The reaction mixture was heated to 75° C. and 1.0 g ammonium persulfate was added to initiate polymerization, which reacted for 2 h. The resulting polymethyl methacrylate (PMMA) coated magnetic fluorescent NPs were harvested by a magnet. With this example synthesis procedure, the weight ratio of magnetic NP/polymer is about 1:1 in the resulting composite particles. Depending on the amount of monomer used during the coating process, the weight ratio of magnetic NP/polymer could be tuned from 9:1 to 1:9.

EXAMPLE 7: FLUORESCENCE ANALYSIS OF RBITC-FUNCTIONALIZED $Fe_3O_4$ COATED NANOPARTICLES

Figure 14:
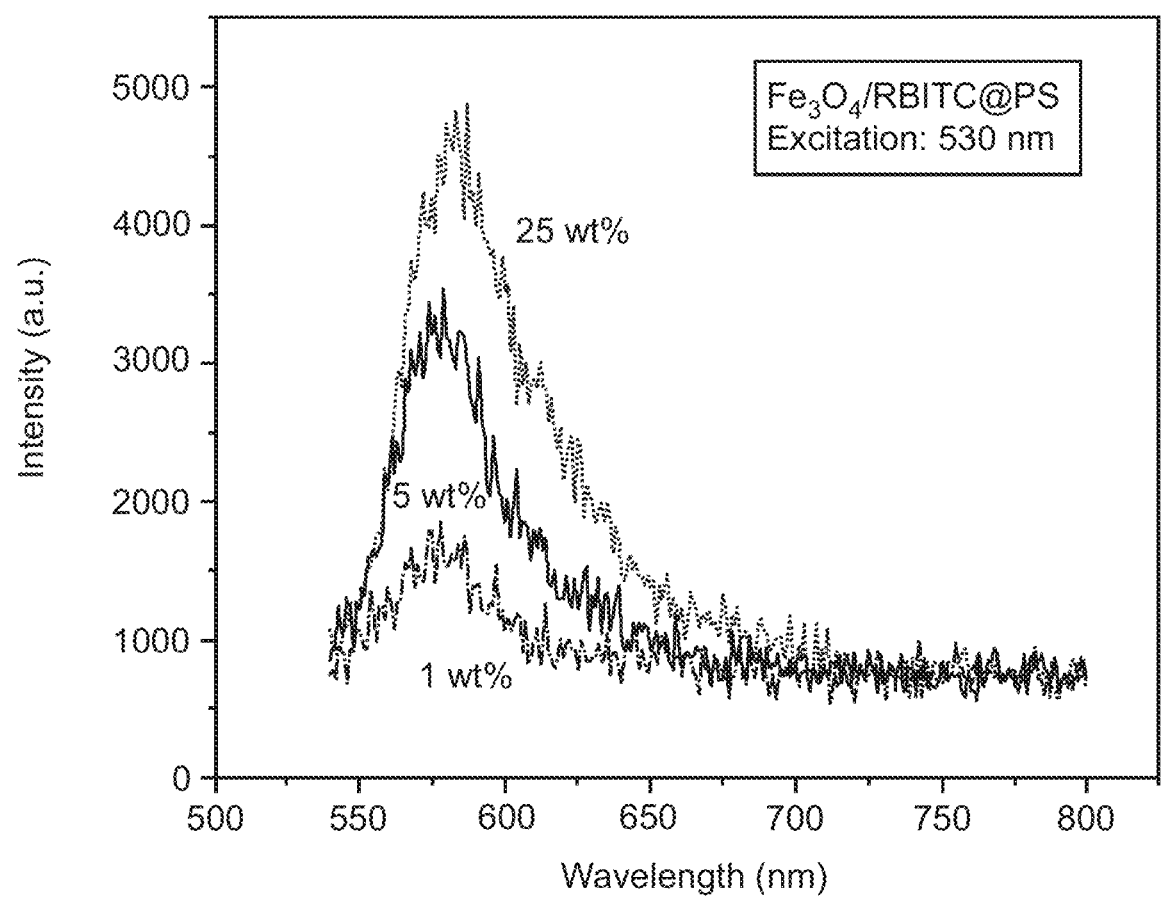
FIG. 14 shows an example fluorescence analysis of RBITC-functionalized $Fe_3O_4$ nanoparticles coated in polystyrene at an excitation wavelength of 530 nm.

FIG. 14 shows an example fluorescence analysis of RBITC-functionalized $Fe_3O_4$ nanoparticles coated in polystyrene at an excitation wavelength of 530 nm. These functionalized, coated nanoparticles were analyzed at a concentration of 1 wt %, 5 wt % and 25 wt % in mud. A tagged mud was prepared by mixing the synthesized RBITC-$_3O_4$-PS nanoparticles and clay powder (bentonite) at 1:99, 5:95 and 25:75 weight ratios, and then 1 g of the mixture was mixed with 10 mL water. The slurry with fluorescent magnetic tags was applied to wet the core when cutting a core of dolomite rock (diameter 3.8 cm) by a Buehler Isomet low speed saw. A piece of the sliced rock was collected and sonicated in 5 mL of water, and then the water suspension was transferred to a quartz cell. For the fluorescence measurement, a neodymium magnet was placed against a wall of the quartz cell to collect the magnet tagged particles for 10 mins, and then the spectra were recorded on the collected particles by a Horiba NanoLog-3 fluorescence spectrometer in a front face reflectance mode at excitation wavelength of 495 nm.

The term "about" as used in this disclosure can allow for a degree of variability in a value or range, for example, within 10%, within 5%, or within 1% of a stated value or of a stated limit of a range.

The term "substantially" as used in this disclosure refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The following units of measure have been mentioned in this disclosure:

| Unit of Measure | Full form |
| --- | --- |
| g | gram |
| mL | milliliter |
| M | molar |
| cm | centimeter |
| nm | nanometer |
| wt % | weight percent |
| ° C. | degrees Celsius |

-continued

| Unit of Measure | Full form |
|---|---|
| min | minute |
| h | hour |

In some implementations, a nanoparticle tag includes a superparamagnetic iron oxide core, an intermediate layer comprising a fluorescent dye, and a polymer shell.

This aspect, taken alone or combinable with any other aspect, can include the following features. The superparamagnetic iron oxide core includes $Fe_3O_4$.

This aspect, taken alone or combinable with any other aspect, can include the following features. The superparamagnetic iron oxide core includes $\gamma$-$Fe_2O_3$. This aspect, taken alone or combinable with any other aspect, can include the
following features. The superparamagnetic iron oxide core includes $CoFe_2O_4$, $NiFe_2O_4$, or $MnFe_2O_4$.

This aspect, taken alone or combinable with any other aspect, can include the following features. The fluorescent dye includes an isothiocyanate functional group. This aspect, taken alone or combinable with any other aspect, can include the
following features. The fluorescent dye includes fluorescein isothiocyanate, Rhodamine B isothiocyanate, tetramethylrhodamine isothiocyanate, or NIR-797, or any combination thereof.

This aspect, taken alone or combinable with any other aspect, can include the following features. The fluorescent dye includes an amine functional group. The fluorescent dye includes Rhodamine 123, Congo Red, or Evans Blue, or any combination thereof.

This aspect, taken alone or combinable with any other aspect, can include the following features. The polymer shell includes styrene-based monomers, methacrylate-based monomers, or amine-based monomers, or any combination thereof.

This aspect, taken alone or combinable with any other aspect, can include the following features. The polymer shell includes monomers selected from the group consisting of styrene, p-methyl styrene, p-methoxy styrene, 2,4-dimethyl styrene, 2,4,6-trimethylstyrene, 4-chlorostyrene, 3-chlorostyrne, 2-chlorostyrene, 4-bromostyrene, 3-bromostyrene, 2-bromostyrene, 4-fluorostyrene, 3-flurostyrene, 2-fluorostyrene, 4-(trifluoromethyl)styrene, 3-(trifluoromethyl)styrene, 2-(trifluoromethyl)styrene, 2,3,4,5,6- pentafluorostyrene, allylbenzene, allylpentafluorobenzene, phenyl methacrylate, hexyl methacrylate, butyl methacrylate, isobutyl methacrylate, propyl methacrylate, vinyl methacrylate, methyl methacrylate, 2-hydroxyethyl methacrylate, pentafluorophenyl methacrylate, allylamine, 3-buten-1-amine, N-allylmethylamine, allylmethylamine, N-vinylformamide, 2-methyl-2-propen-1-amine, and 2-methylallylamine, or any combination thereof.

This aspect, taken alone or combinable with any other aspect, can include the following features. The weight ratio of the superparamagnetic iron oxide core to the polymer is from 9:1 to 1:9.

This aspect, taken alone or combinable with any other aspect, can include the following features. The weight ratio of the superparamagnetic iron oxide core to the polymer is 1:1.

In some implementations, a method of making a nanoparticle tag includes providing a superparamagnetic iron oxide nanoparticle core, functionalizing the surface of the superparamagnetic iron oxide nanoparticle core to yield a functionalized nanoparticle core, and covalently bonding a fluorescent dye to the functionalized nanoparticle core.

This aspect, taken alone or combinable with any other aspect, can include the following features. The method includes covalently bonding a polymer to the functionalized nanoparticle core.

This aspect, taken alone or combinable with any other aspect, can include the following features. The polymer includes styrene-based monomers, methacrylate-based monomers, or amine-based monomers, or any combination thereof.

This aspect, taken alone or combinable with any other aspect, can include the following features. The polymer includes monomers selected from the group consisting of styrene, p-methyl styrene, p-methoxystyrene, 2,4-dimethyl styrene, 2,4,6-trimethylstyrene, 4-chlorostyrene, 3-chlorostyrene, 2-chlorostyrene, 4-bromostyrene, 3-bromostyrene, 2-bromostyrene, 4-fluorostyrene, 3-fluorostyrene, 2-fluorostyrene, 4-(trifluoromethyl)styrene, 3-(trifluoromethyl)styrene, 2-(trifluoromethyl)styrene, 2,3,4,5,6-pentafluorostyrene, allylbenzene, allylpentafluorobenzene, phenyl methacrylate, hexyl methacrylate, butyl methacrylate, isobutyl methacrylate, propyl methacrylate, vinyl methacrylate, methyl methacrylate, 2-hydroxyethyl methacrylate, pentafluorophenyl methacrylate, allylamine, 3-buten-1-amine, N-allylmethylamine, allylmethylamine, N-vinylformamide, 2-methyl-2-propen-1-amine, and 2-methylallylamine, or any combination thereof.

This aspect, taken alone or combinable with any other aspect, can include the following features. The weight ratio of the superparamagnetic iron oxide core to the polymer is from 9:1 to 1:9.

This aspect, taken alone or combinable with any other aspect, can include the following features. The weight ratio of the superparamagnetic iron oxide core to the polymer is 1:1.

This aspect, taken alone or combinable with any other aspect, can include the following features. The superparamagnetic iron oxide nanoparticle core includes $Fe_3O_4$.

This aspect, taken alone or combinable with any other aspect, can include the following features. The superparamagnetic iron oxide nanoparticle core includes $\gamma$-$Fe_2O_3$.

This aspect, taken alone or combinable with any other aspect, can include the following features. The superparamagnetic iron oxide nanoparticle core includes $CoFe_2O_4$, $NiFe_2O_4$, or $MnFe_2O_4$.

This aspect, taken alone or combinable with any other aspect, can include the following features. Functionalizing the surface of the superparamagnetic iron oxide nanoparticle core includes functionalizing the surface of the superparamagnetic iron oxide core with polyethylenimine groups, allyl groups, or epoxy groups, or any combination thereof.

This aspect, taken alone or combinable with any other aspect, can include the following features. Functionalizing the surface of the superparamagnetic iron oxide core with polyethylenimine groups, allyl groups, or epoxy groups, or any combination thereof includes functionalizing the surface of the superparamagnetic iron oxide core with trimethoxysilylpropyl modified polyethylenimine, 3-(trimethoxysilyl) propyl methacrylate, or glycidoxypropyltrimethoxysilane, or any combination thereof.

This aspect, taken alone or combinable with any other aspect, can include the following features. The fluorescent dye includes an isothiocyanate functional group.

This aspect, taken alone or combinable with any other aspect, can include the following features. The fluorescent dye includes fluorescein isothiocyanate, Rhodamine B isothiocyanate, tetramethylrhodamine isothiocyanate, or NIR-797, or any combination thereof.

This aspect, taken alone or combinable with any other aspect, can include the following features. The fluorescent dye includes an amine functional group.

This aspect, taken alone or combinable with any other aspect, can include the following features. The fluorescent dye comprises Rhodamine 123, Congo Red, or Evans Blue, or any combination thereof.

In some implementations, a method of determining the origin location of a subterranean sample includes mixing a nanoparticle tag into a fluid, wherein the nanoparticle tag includes a superparamagnetic iron oxide core, an intermediate layer comprising a fluorescent dye, and a polymer shell. The method includes flowing the fluid through a work string into a subterranean formation, recovering subterranean samples from the subterranean formation, separating tagged samples from untagged samples using a magnet, and determining an origin location of the subterranean sample by analyzing the fluorescent signal of the nanoparticle tag.

This aspect, taken alone or combinable with any other aspect, can include the following features. The method includes analyzing the polymer shell of the nanoparticle tag with mass spectroscopy.

This aspect, taken alone or combinable with any other aspect, can include the following features. Analyzing the polymer shell with mass spectroscopy includes analyzing the polymer shell with pyrolysis-gas chromatography-mass spectrometry.

This aspect, taken alone or combinable with any other aspect, can include the following features. The method includes washing the subterranean sample with water before determining the origin location of the subterranean sample.

This aspect, taken alone or combinable with any other aspect, can include the following features. The method includes removing unbound tags from the fluid using a magnet.

The term "solvent" as used in this disclosure refers to a liquid that can dissolve a solid, another liquid, or a gas to form a solution. Non-limiting examples of solvents are silicones, organic compounds, water, alcohols, ionic liquids, and supercritical fluids.

The term "room temperature" as used in this disclosure refers to a temperature of about 15 degrees Celsius (° C.) to about 28° C.

The term "downhole" as used in this disclosure refers to under the surface of the earth, such as a location within or fluidly connected to a wellbore.

As used in this disclosure, the term "drilling fluid" refers to fluids, slurries, or muds used in drilling operations downhole, such as during the formation of the wellbore.

As used in this disclosure, the term "fracturing fluid" refers to fluids or slurries used downhole during fracturing operations.

As used in this disclosure, the term "fluid" refers to liquids and gels, unless otherwise indicated.

As used in this disclosure, the term "subterranean material" or "subterranean zone" refers to any material under the surface of the earth, including under the surface of the bottom of the ocean. For example, a subterranean zone or material can be any section of a wellbore and any section of a subterranean petroleum- or water-producing formation or region in fluid contact with the wellbore. Placing a material in a subterranean zone can include contacting the material with any section of a wellbore or with any subterranean region in fluid contact the material. Subterranean materials can include any materials placed into the wellbore such as cement, drill shafts, liners, tubing, casing, or screens; placing a material in a subterranean zone can include contacting with such subterranean materials. In some examples, a subterranean zone or material can be any downhole region that can produce liquid or gaseous petroleum materials, water, or any downhole section in fluid contact with liquid or gaseous petroleum materials, or water. For example, a subterranean zone or material can be at least one of an area desired to be fractured, a fracture or an area surrounding a fracture, and a flow pathway or an area surrounding a flow pathway, in which a fracture or a flow pathway can be optionally fluidly connected to a subterranean petroleum- or water-producing region, directly or through one or more fractures or flow pathways.

As used in this disclosure, "treatment of a subterranean zone" can include any activity directed to extraction of water or petroleum materials from a subterranean petroleum- or water-producing formation or region, for example, including drilling, stimulation, hydraulic fracturing, clean-up, acidizing, completion, cementing, remedial treatment, abandonment, aquifer remediation, identifying oil rich regions via imaging techniques, and the like.

As used in this disclosure, a "flow pathway" downhole can include any suitable subterranean flow pathway through which two subterranean locations are in fluid connection. The flow pathway can be sufficient for petroleum or water to flow from one subterranean location to the wellbore or vice-versa. A flow pathway can include at least one of a hydraulic fracture, and a fluid connection across a screen, across gravel pack, across proppant, including across resin-bonded proppant or proppant deposited in a fracture, and across sand. A flow pathway can include a natural subterranean passageway through which fluids can flow. In some implementations, a flow pathway can be a water source and can include water. In some implementations, a flow pathway can be a petroleum source and can include petroleum. In some implementations, a flow pathway can be sufficient to divert water, a downhole fluid, or a produced hydrocarbon from a wellbore, fracture, or flow pathway connected to the pathway.

As used in this disclosure, "weight percent" (wt %) can be considered a mass fraction or a mass ratio of a substance to the total mixture or composition. Weight percent can be a weight-to-weight ratio or mass-to-mass ratio, unless indicated otherwise.

A number of implementations of the disclosure have been described. Nevertheless, it will be understood that various modifications may be made without departing from the spirit and scope of the disclosure.

What is claimed is:

1. A method of making a nanoparticle tag, comprising:
providing a superparamagnetic iron oxide nanoparticle core;
functionalizing the surface of the superparamagnetic iron oxide nanoparticle core with polyethylenimine groups to yield a functionalized nanoparticle core; and
covalently bonding a fluorescent dye to the functionalized nanoparticle core, wherein the fluorescent dye comprises an isothiocyanate functional group and wherein the fluorescent dye is covalently bound to the polyethylenimine through the isothiocyanate function group to yield a thiourea.

2. The method of claim 1, further comprising covalently bonding a polymer to the functionalized nanoparticle core.

3. The method of claim 2, wherein the polymer comprises styrene-based monomers, methacrylate-based monomers, or amine-based monomers, or any combination thereof.

4. The method of claim 3, wherein the polymer comprises monomers selected from the group consisting of styrene, p-methylstyrene, p-methoxystyrene, 2,4-dimethylstyrene, 2,4,6-trimethylstyrene, 4-chlorostyrene, 3-chlorostyrene, 2-chlorostyrene, 4-bromostyrene, 3-bromostyrene, 2-bromostyrene, 4-fluorostyrene, 3-fluorostyrene, 2-fluorostyrene, 4-(trifluoromethyl)styrene, 3-(trifluoromethyl)styrene, 2-(trifluoromethyl)styrene, 2,3,4,5,6-pentafluorostyrene, allylbenzene, allylpentafluorobenzene, phenyl methacrylate, hexyl methacrylate, butyl methacrylate, isobutyl methacrylate, propyl methacrylate, vinyl methacrylate, methyl methacrylate, 2-hydroxyethyl methacrylate, pentafluorophenyl methacrylate, allylamine, 3-buten-1-amine, N-allylmethylamine, allylmethylamine, N-vinylformamide, 2-methyl-2-propen-1-amine, and 2-methylallylamine, or any combination thereof.

5. The method of claim 2, wherein the weight ratio of the superparamagnetic iron oxide core to the polymer is from 9:1 to 1:9.

6. The method of claim 5, wherein the weight ratio of the superparamagnetic iron oxide core to the polymer is 1:1.

7. The method of claim 1, wherein the superparamagnetic iron oxide nanoparticle core comprises $Fe_3O_4$.

8. The method of claim 1, wherein the superparamagnetic iron oxide nanoparticle core comprises $\gamma\text{-}Fe_2O_3$.

9. The method of claim 1, wherein the superparamagnetic iron oxide nanoparticle core comprises $CoFe_2O_4$, $NiFe_2O_4$, or $MnFe_2O_4$.

10. The method of claim 1, wherein functionalizing the surface of the superparamagnetic iron oxide nanoparticle core further comprises functionalizing the surface of the superparamagnetic iron oxide core with allyl groups, or epoxy groups, or any combination thereof.

11. The method of claim 1, wherein functionalizing the surface of the superparamagnetic iron oxide core with polyethylenimine groups comprises functionalizing the surface of the superparamagnetic iron oxide core with trimethoxysilylpropyl modified polyethylenimine.

12. The method of claim 1, wherein the fluorescent dye comprises fluorescein isothiocyanate, Rhodamine B isothiocyanate, tetramethylrhodamine isothiocyanate, or NIR-797, or any combination thereof.

13. The method of claim 1, wherein the nanoparticle tag further comprises a second fluorescent dye, wherein the second fluorescent dye comprises an amine functional group.

14. The method of claim 13, wherein the second fluorescent dye comprises Rhodamine 123, Congo Red, or Evans Blue, or any combination thereof.

15. A method of determining the origin location of a subterranean sample, comprising:
mixing a nanoparticle tag into a fluid, wherein the nanoparticle tag comprises a superparamagnetic iron oxide core wherein the superparamagnetic iron oxide core is functionalized with polyethylenimine, an intermediate layer comprising a fluorescent dye wherein the fluorescent dye comprises an isothiocyanate function group and the fluorescent dye is covalently bound to the polyethylenimine through the isothiocyanate functional group to yield a thiourea, and a polymer shell;
flowing the fluid through a work string into a subterranean formation;
recovering subterranean samples from the subterranean formation;
separating tagged samples from untagged samples using a magnet; and
determining an origin location of the subterranean sample by analyzing the fluorescent signal of the nanoparticle tag.

16. The method of claim 15, further comprising analyzing the polymer shell of the nanoparticle tag with mass spectroscopy.

17. The method of claim 16, wherein analyzing the polymer shell with mass spectroscopy comprises analyzing the polymer shell with pyrolysis-gas chromatography-mass spectrometry.

18. The method of claim 15, further comprising washing the subterranean sample with water before determining the origin location of the subterranean sample.

19. The method of claim 15, further comprising removing unbound tags from the fluid using a magnet.

20. The method of claim 10, wherein functionalizing the surface of the superparamagnetic iron oxide core with allyl groups, or epoxy groups, or any combination thereof further comprises functionalizing the surface of the superparamagnetic iron oxide core with 3-(trimethoxysilyl)propyl methacrylate, or glycidoxypropyltrimethoxysilane, or any combination thereof.

* * * * *